United States Patent
Suzuki et al.

(10) Patent No.: US 11,965,125 B2
(45) Date of Patent: *Apr. 23, 2024

(54) COMPOUND, LIQUID CRYSTAL COMPOSITION, CURED PRODUCT, OPTICALLY ANISOTROPIC BODY, AND REFLECTIVE FILM

(71) Applicant: FUJIFILM Corporation, Tokyo (JP)

(72) Inventors: Yuko Suzuki, Minamiashigara (JP); Keisuke Kodama, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

This patent is subject to a terminal disclaimer.

(21) Appl. No.: 17/587,724

(22) Filed: Jan. 28, 2022

(65) Prior Publication Data
US 2022/0145181 A1    May 12, 2022

Related U.S. Application Data

(63) Continuation of application No. PCT/JP2020/027402, filed on Jul. 14, 2020.

(30) Foreign Application Priority Data

Jul. 29, 2019  (JP) .................. 2019-138845

(51) Int. Cl.
C09K 19/04    (2006.01)
G02B 5/30     (2006.01)

(52) U.S. Cl.
CPC ........ C09K 19/0403 (2013.01); G02B 5/3016 (2013.01); C09K 2019/0407 (2013.01); C09K 2019/0414 (2013.01); C09K 2019/0448 (2013.01); C09K 2219/03 (2013.01)

(58) Field of Classification Search
CPC ........................................... C09K 19/54
See application file for complete search history.

(56) References Cited

U.S. PATENT DOCUMENTS

| | | | |
|---|---|---|---|
| 2008/0090026 A1* | 4/2008 | Bernatz ............. | C09K 19/322 560/76 |
| 2014/0160420 A1* | 6/2014 | Wang ................ | G02F 1/13718 349/176 |
| 2014/0264168 A1 | 9/2014 | Dunn et al. | |
| 2019/0055180 A1* | 2/2019 | Nishida ............ | C07C 39/17 |
| 2020/0071615 A1* | 3/2020 | Kodama .......... | G02F 1/133553 |
| 2020/0231874 A1 | 7/2020 | Katoh et al. | |
| 2020/0409202 A1 | 12/2020 | Kodama et al. | |
| 2021/0198230 A1 | 7/2021 | Suzuki et al. | |

FOREIGN PATENT DOCUMENTS

| | | | |
|---|---|---|---|
| CN | 105456040 A | * | 4/2016 |
| JP | 2008-116931 A | | 5/2008 |
| JP | 2018-90560 A | | 6/2018 |
| JP | 2018090560 A | * | 6/2018 ............ C07C 37/48 |
| JP | 7064575 B2 | | 5/2022 |
| JP | 7181301 B2 | | 11/2022 |
| WO | WO 2018/194157 A1 | | 10/2018 |
| WO | WO-2018194157 A1 | * | 10/2018 .......... C07C 233/55 |
| WO | WO 2019/069911 A1 | | 4/2019 |
| WO | WO 2019/181433 A1 | | 9/2019 |
| WO | WO 2019/182052 A1 | | 9/2019 |
| WO | WO 2020/049957 A1 | | 3/2020 |

OTHER PUBLICATIONS

Briza et al. ("Chromophoric Binaphthyl Derivatives", Organic letters, 2005, 7 (17), 3661-3664). (Year: 2005).*
Kickova et al. ("Synthesis and properties of macrocyclic diazene switch with binaphthalene unit attached via acrylamide linkers", Chemical Papers, 2013, 67 (1), 101-109). (Year: 2013).*
Japanese Notice of Reasons for Refusal for corresponding Japanese Application No. 2021-536909, dated Jan. 17, 2023, with an English translation.
Bříza et al., "Chromophoric Binaphthyl Derivatives," Organic Letters, vol. 7, No. 17, 2005, pp. 3661-3664, 4 pages total.
Costantino et al., "Efficient Routes to Racemic and Enantiomerically Pure (S)-BINOL Diesters," Synthetic Communications, vol. 43, No. 23, 2013, pp. 3192-3202, 12 pages total.
International Preliminary Report on Patentability and Written Opinion of the International Searching Authority (Forms PCT/IB/326, PCT/IB/373, and PCT/ISA/237) for International Application No. PCT/JP2020/027402, dated Feb. 10, 2022, with an English translation.
International Search Report (Form PCT/ISA/210) for International Application No. PCT/JP2020/027402, dated Sep. 29, 2020, with an English translation.
Kicková et al., "Synthesis and properties of macrocyclic diazene switch with binaphthalene unit attached via acrylamide linkers," Chemical Papers, vol. 67, No. 1, 2013, pp. 101-109, 9 pages total.
Tanaka et al., "1,1'-Binaphthalene-2,2'-diol as a Chiral Auxiliary. Diastereoselective Alkylation of Binaphthyl Esters, Complex-Induced Proximity Effects in Enolate Formation, and One-Step Synthesis of an Optically Active β-Substituted Ketone," Journal of the American Chemical Society, vol. 117, No. 49, 1995, pp. 12159-12171, 13 pages total.

* cited by examiner

*Primary Examiner* — Chanceity N Robinson
(74) *Attorney, Agent, or Firm* — Birch, Stewart, Kolasch & Birch, LLP

(57) ABSTRACT

A compound has an excellent rate of change in HTP caused by exposure. A liquid crystal composition is formed of the compound. A cured product, an optically anisotropic body, and a reflective film can be obtained by curing the liquid crystal composition. The compound is represented by General Formula (1):

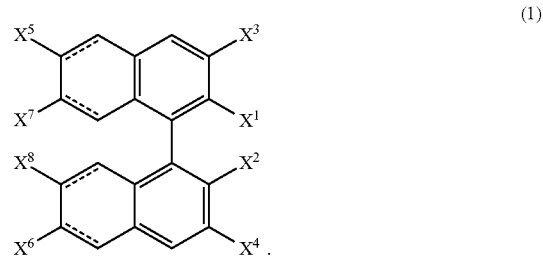

15 Claims, No Drawings

COMPOUND, LIQUID CRYSTAL COMPOSITION, CURED PRODUCT, OPTICALLY ANISOTROPIC BODY, AND REFLECTIVE FILM

CROSS-REFERENCE TO RELATED APPLICATIONS

This application is a Continuation of PCT International Application No. PCT/JP2020/027402 filed on Jul. 14, 2020, which claims priority under 35 U.S.C. § 119(a) to Japanese Patent Application No. 2019-138845 filed on Jul. 29, 2019. The above application is hereby expressly incorporated by reference, in its entirety, into the present application.

BACKGROUND OF THE INVENTION

1. Field of the Invention

The present invention relates to a compound, a liquid crystal composition, a cured product, an optically anisotropic body, and a reflective film.

2. Description of the Related Art

A compound exhibiting liquid crystallinity (hereinafter, also referred to as a "liquid crystalline compound") can be applied to various uses. For example, the liquid crystalline compound is applied to the manufacturing of an optically anisotropic body typified by a retardation film, or to the manufacturing of a reflective film obtained by immobilizing a cholesteric liquid crystalline phase.

Generally, the cholesteric liquid crystalline phase is formed by adding a chiral compound to a nematic liquid crystal. US2014/0264168A discloses a chiral compound having a helical twisting power (HTP) to the liquid crystalline compound.

SUMMARY OF THE INVENTION

On the other hand, in recent years, there is a demand for a chiral compound which can optionally change HTP by performing a certain treatment. For example, a chiral compound which greatly changes the intensity of HTP caused by exposure to light irradiation such as ultraviolet rays has been desired.

As a result of studies on the chiral compound disclosed in US2014/0264168A, the present inventors have found that, in the chiral compound disclosed in US2014/0264168A, the degree of change in intensity of HTP (hereinafter, also referred to as a "rate of change in HTP) caused by exposure to light irradiation such as ultraviolet rays does not reach the level currently desired.

Therefore, an object of the present invention is to provide a compound having an excellent rate of change in HTP caused by exposure.

Another object of the present invention is to provide a liquid crystal composition formed of the compound, a cured product, an optically anisotropic body, and a reflective film.

The present inventors have found that the above-described objects can be achieved by a compound represented by General Formula (1) described later, and have completed the present invention.

That is, the present inventors have found that the above-described object can be achieved by the following configuration.

[1] A compound represented by General Formula (1) described later.

[2] The compound according to [1],
in which, in General Formula (1), at least one of the substituents including the group represented by General Formula (2) is linked to a binaphthyl skeleton site specified in General Formula (1) at the bonding position represented by *1.

[3] The compound according to [1] or [2],
in which, in General Formula (1), $X^1$ and $X^2$ are linked to each other to form a ring.

[4] The compound according to [1] or [2],
in which, in General Formula (1), both $X^1$ and $X^2$ represent the substituent including the group represented by General Formula (2), and
at least one of the substituents including the group represented by General Formula (2) is linked to a binaphthyl skeleton site specified in General Formula (1) at the bonding position represented by *1.

[5] The compound according to any one of [1] to [4],
in which, in General Formula (2), Z is a single bond, and a carbonyl carbon specified in General Formula (2) is not bonded to —O—.

[6] The compound according to [5],
in which the substituent including the group represented by General Formula (2) is a substituent including a group represented by General Formula (3) described later.

[7] A liquid crystal composition comprising:
the compound according to any one of [1] to [6]; and
a liquid crystalline compound.

[8] The liquid crystal composition according to [7],
in which the liquid crystalline compound includes two polymerizable groups.

[9] A cured product obtained by curing the liquid crystal composition according to [7] or [8].

[10] An optically anisotropic body obtained by curing the liquid crystal composition according to [7] or [8].

[11] A reflective film obtained by curing the liquid crystal composition according to [7] or [8].

According to the present invention, it is possible to provide a compound having an excellent rate of change in HTP caused by exposure.

In addition, according to the present invention, it is possible to provide a liquid crystal composition formed of the compound, a cured product, an optically anisotropic body, and a reflective film.

DESCRIPTION OF THE PREFERRED EMBODIMENTS

Hereinafter, the present invention will be described in detail.

The description of the constitutional requirements described below is made on the basis of representative embodiments of the present invention, but it should not be construed that the present invention is limited to those embodiments.

In the present specification, a numerical range represented using "to" means a range including numerical values described before and after the preposition "to" as a lower limit value and an upper limit value.

In addition, in the present specification, "(meth)acrylate" is a notation representing both acrylate and methacrylate.

In a notation for a group (atomic group) in the present specification, in a case where the group is denoted without specifying whether it is substituted or unsubstituted, the group includes both a group having no substituent and a group having a substituent. For example, "alkyl group" denotes not only an alkyl group having no substituent (unsubstituted alkyl group) but also an alkyl group having a substituent (substituted alkyl group).

In the present specification, in a case of simply referring to a substituent, examples of the substituent include the following substituent T.

Substituent T

Examples of the substituent T include a halogen atom (a fluorine atom, a chlorine atom, a bromine atom, an iodine atom, and the like), an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an awl or heterocyclic azo group, an imido group, a phosphino group, a phosphinyl group, a phosphinyloxy group, a phosphinylamino group, a silyl group, and a group including a polymerizable group (as a suitable specific example, a group represented by General Formula (T) and the like).

*-$L_T$-$P_T$    General Formula (T)

In General Formula (T), $L_T$ represents a single bond or a divalent linking group. $P_T$ represents a polymerizable group represented by General Formulae (P-1) to (P-20) described below.

The divalent linking group represented by $L_T$ is not particularly limited, and an alkylene group which may include a hetero atom is preferable, an alkylene group having 1 to 10 carbon atoms, which may include an oxygen atom, is more preferable, and an alkylene group having 1 to 6 carbon atoms, which may include an oxygen atom, is still more preferable.

In General Formulae (P-1) to (P-20) shown below, * represents a bonding position. In addition, Ra represents a hydrogen atom or a methyl group. In addition, Me represents a methyl group, and Et represents an ethyl group.

(P-1)

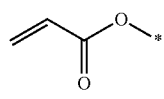

(P-2)

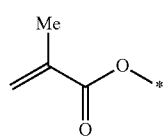

(P-3)

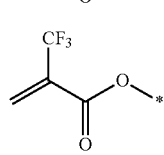

(P-4)

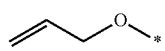

(P-5)

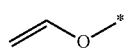

(P-6)

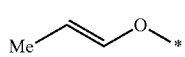

(P-7)

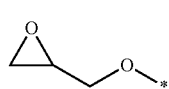

(P-8)

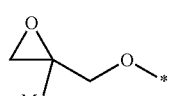

(P-9)

(P-10)

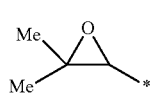

(P-11)

(P-12)

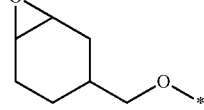

(P-13)

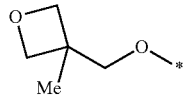

(P-14)

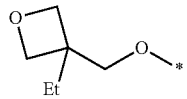

(P-15)

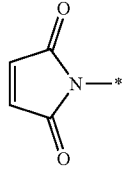

(P-16)

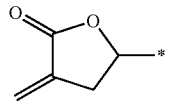

(P-17)

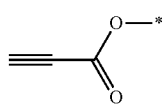

-continued

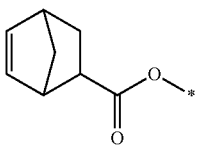
(P-18)

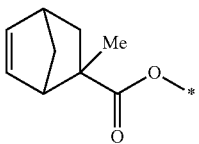
(P-19)

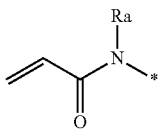
(P-20)

Among the above-described substituents, a substituent having a hydrogen atom may be further substituted with any one of the above-described substituents in the portion of the hydrogen atom in the substituent.

The bonding direction of a divalent group denoted in the present specification is not limited unless otherwise specified. For example, in a compound represented by the General Formula "L-M-N", in a case where M is —OCO—C(CN)=CH—, and the position bonded to the L side is defined as *1 and the position bonded to the N side is defined as *2, M may be *1—OCO—C(CN)=CH—*2 or *1—CH=C(CN)—COO—*2. In addition, for example, in a case where M is —COO—, and the position bonded to the L side is defined as *1 and the position bonded to the N side is defined as *2, M may be *1—COO—*2 or *1—OCO—*2.

Compound Represented by General Formula (1)

As a feature of a compound (hereinafter, also referred to as a "specific compound") represented by General Formula (1), at least one of $X^1$, $X^3$, $X^5$, or $X^7$ and at least one of $X^2$, $X^4$, $X^6$, or $X^8$ are a substituent including a group represented by General Formula (2) described later.

In the substituent including a group represented by General Formula (2) described later, in a case where a double bonding site specified in General Formula (2) is irradiated with energy such as ultraviolet rays, the double bonding site may be photoisomerized and cause a structural change. That is, the group represented by General Formula (2) has $Y^1$ and $Y^2$ on the same side with the double bond specified in General Formula (2) as an axis, and in a case of being irradiated with energy such as ultraviolet rays, structural change can occur by photoisomerizing $Y^1$ and $Y^2$ so that $Y^1$ and $Y^2$ are on different sides of the axis of the double bond. In the specific compound, it is presumed that the structural change due to the photoisomerization is large and a dihedral angle of a binaphthyl skeleton site is easily changed by the photoisomerization, and as a result, an excellent rate of change in HTP is achieved.

In the present specification, the "binaphthyl skeleton site" means a structural site (structural site shown below) of General Formula (1) described later, excluding $X^1$ to $X^8$. That is, the "binaphthyl skeleton" generically corresponds to structural sites of General Formula (1-1) and General Formula (1-2) described later, excluding $X^1$ to $X^8$.

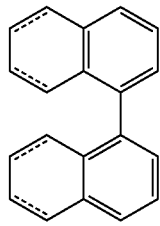

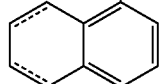

Hereinafter, the specific compound will be described in detail.

The specific compound is a compound represented by General Formula (1).

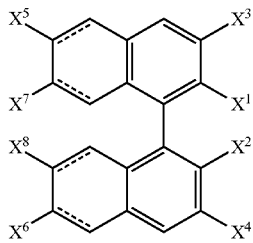
(1)

In General Formula (1), a portion where a solid line and a broken line are parallel to each other represents a single bond or a double bond. For example, in the compound represented by General Formula (1), in a case where the portion where the solid line and the broken line are parallel to each other is a single bond, the compound represented by General Formula (1) corresponds to a compound represented by General Formula (1-1), and in a case where the portion where the solid line and the broken line are parallel to each other is a double bond, the compound represented by General Formula (1) corresponds to a compound represented by General Formula (1-2).

Among these, as the specific compound, the compound represented by General Formula (1-2) is preferable.

$X^1$ to $X^8$ in General Formula (1-1) and General Formula (1-2) respectively have the same meaning as $X^1$ to $X^8$ in General Formula (1).

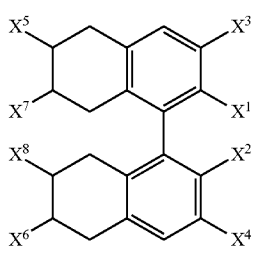
(1-1)

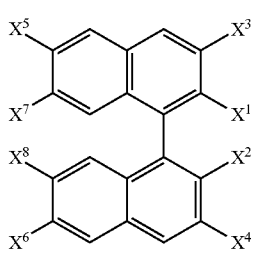
(1-2)

In General Formula (1), $X^1$ to $X^8$ each independently represent a hydrogen atom or a monovalent substituent.

The substituent represented by $X^1$ to $X^8$ is not particularly limited, and examples thereof include groups exemplified as the above-described substituent T. However, at least one of $X^1$, $X^3$, $X^5$, or $X^7$ and at least one of $X^2$, $X^4$, $X^6$, or $X^8$ represent a substituent including a group represented by General Formula (2) described later. From the viewpoint that the rate of change in HTP is more excellent, it is preferable that any combination selected from $X^1$ and $X^2$, $X^3$ and $X^4$, $X^5$ and $X^6$, or $X^7$ and $X^8$ represents the substituent including a group represented by General Formula (2) described later.

Among these, from the viewpoint that the rate of change in HTP is more excellent, in General Formula (1), it is preferable that $X^1$ and $X^2$ are linked to each other to form a ring. That is, in General Formula (1), it is preferable that $X^1$ and $X^2$ are linked to each other to form a ring, and at least one of $X^3$, $X^5$, or $X^7$ and at least one of $X^4$, $X^6$, or $X^8$ represent the substituent including a group represented by General Formula (2) described later.

The ring bonded by linking $X^1$ and $X^2$ to each other is not particularly limited, and may be either an aromatic ring or a non-aromatic ring, but a non-aromatic ring is preferable.

In a case where $X^1$ and $X^2$ are linked to each other to form a ring, the group formed by linking $X^1$ and $X^2$ to each other is preferably, for example, *-$L^{S1}$-divalent aromatic hydrocarbon ring group-$L^{S2}$-* or *-$L^{S3}$-divalent aliphatic hydrocarbon group-$L^{S4}$-*. * represents a bonding position to the binaphthyl skeleton in. General Formula (1).

Examples of an aromatic hydrocarbon ring constituting the above-described divalent aromatic hydrocarbon ring group include a benzene ring and a naphthalene ring.

The above-described divalent aliphatic hydrocarbon group may be linear, branched, or cyclic. The number of carbon atoms is preferably 1 to 12, more preferably 1 to 10, and still more preferably 1 to 6. As the aliphatic hydrocarbon group, an alkylene group is preferable. A hydrogen atom in the aliphatic hydrocarbon group may be replaced with another substituent such as a halogen atom.

$L^{S1}$ to $L^{S4}$ each independently represent a single bond or a divalent linking group.

The divalent linking group represented by $L^{S1}$ and $L^{S2}$ is not particularly limited, and examples thereof include a divalent aliphatic hydrocarbon group (which may be linear, branched, or cyclic; a divalent aliphatic hydrocarbon group having 1 to 20 carbon atoms is preferable, and examples thereof include an alkylene group, an alkenylene group, and an alkynylene group), —O—, —S—, —$SO_2$—, —$NR^D$—, —CO—, —N=N—, —CH=N—, and a group of a combination of two or more these groups. Here, $R^D$ represents a hydrogen atom or an alkyl group (preferably having 1 to 10 carbon atoms).

A hydrogen atom in the above-described divalent linking group may be replaced with another substituent such as a halogen atom.

As $L^{S1}$ and $L^{S2}$, a single bond, a divalent aliphatic hydrocarbon group (which may be linear, branched, or cyclic; a divalent aliphatic hydrocarbon group having 1 to 20 carbon atoms is preferable, and examples thereof include an alkylene group, an alkenylene group, and an alkynylene group), —O—, —CO—, —CO—NH—, —$CH_2$O—, or —COO— is preferable.

The divalent linking group represented by $L^{S3}$ and $L^{S4}$ is not particularly limited, and examples thereof include a divalent arylene group (preferably a phenylene group), —O—, —S—, —$SO_2$—, —$NR^D$—, —CO—, —N=N—, —CH=N—, and a group of a combination of two or more these groups. Here, $R^D$ represents a hydrogen atom or an alkyl group (preferably having 1 to 10 carbon atoms).

A hydrogen atom in the above-described divalent linking group may be replaced with another substituent such as a halogen atom.

As $L^{S3}$ and $L^{S4}$, a single bond, —O—, —CO—, —CO—NH—, or —COO— is preferable.

In General Formula (1), in a case where $X^1$ and $X^2$ are not linked to each other, from the viewpoint that the rate of change in HTP is more excellent, it is preferable that both $X^1$ and $X^2$ represent the substituent including the group represented by General Formula (2), and at least one of the substituents including the group represented by General Formula (2) (preferably, all substituents) is linked to a binaphthyl skeleton site specified in General Formula (1) at the bonding position represented by *1 in the substituent.

Hereinafter, the substituent including a group represented by General Formula (2) will be described.

First, the group represented by General Formula (2) will be described.

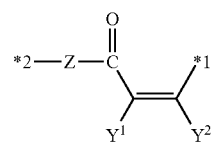

(2)

In General Formula (2), Z represents a single bond or —O—. $Y^1$ and $Y^2$ each independently represent a hydrogen atom or a hydrocarbon group not including an aryl group.

As Z, from the viewpoint that the rate of change in HTP is more excellent, a single bond is preferable.

Specific examples of the hydrocarbon group not including an aryl group, which is represented by $Y^1$ and $Y^2$, include an aliphatic hydrocarbon group. The above-described aliphatic hydrocarbon group may have a substituent. Examples of the substituent include groups exemplified as the above-described substituent T. The above-described aliphatic hydrocarbon group does not have an aryl group as the substituent.

The aliphatic hydrocarbon group may be linear, branched, or cyclic.

In addition, the aliphatic hydrocarbon group may be a saturated aliphatic hydrocarbon group or an unsaturated aliphatic hydrocarbon group. In a case where the above-described aliphatic hydrocarbon group represents an unsaturated aliphatic hydrocarbon group, the aliphatic hydrocarbon group may have both a double bond and a triple bond.

In a case where the above-described aliphatic hydrocarbon group represents an alkenyl group, the number of double bonds in the alkenyl group may be one or two or more.

In a case where the above-described aliphatic hydrocarbon group represents an alkynyl group, the number of triple bonds in the alkynyl group may be one or two or more.

In a case where the above-described aliphatic hydrocarbon group is an alkyl group, from the viewpoint that the rate of change in HTP is more excellent, the number of carbon atoms in the alkyl group is preferably 1 to 10, more preferably 1 to 6, and still more preferably 1 to 3.

In a case where the above-described aliphatic hydrocarbon group is an alkenyl group, from the viewpoint that the rate of change in HTP is more excellent, the number of carbon atoms in the alkenyl group is preferably 2 to 10, more preferably 2 to 6, and still more preferably 2 or 3.

In a case where the above-described aliphatic hydrocarbon group is an alkynyl group, from the viewpoint that the rate of change in HTP is more excellent, the number of carbon atoms in the alkynyl group is preferably 2 to 10, more preferably 2 to 6, and still more preferably 2 or 3.

From the viewpoint that the rate of change in HTP is more excellent, it is preferable that both $Y^1$ and $Y^2$ are hydrogen atoms.

In General Formula (2), *1 and *2 represent bonding positions.

As the group represented by General Formula (2), in a case where *1 is a bonding position, a group represented by General Formula (2A) is preferable, and in a case where *2 is a bonding position, a group represented by General Formula (2B) is preferable. Among these, as the group represented by General Formula (2), a group represented by General Formula (2A) is more preferable.

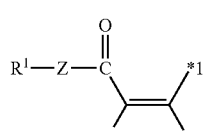

(2A)

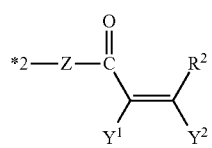

(2B)

$Z$, $Y^1$, $Y^2$, and *1 in General Formula (2A) have the same meaning as $Z$, $Y^1$, $Y^2$, and *1 in General Formula (2), and the preferred aspects are also the same.

$R^1$ represents a hydrogen atom or a substituent. The substituent represented by $R^1$ is not particularly limited, and examples thereof include groups exemplified as the above-described substituent T.

Among these, as the substituent represented by $R^1$, an aliphatic hydrocarbon group or an aromatic hydrocarbon ring group is preferable.

The above-described aliphatic hydrocarbon group may be linear, branched, or cyclic. The number of carbon atoms is preferably 1 to 12, more preferably 1 to 10, and still more preferably 1 to 6. As the aliphatic hydrocarbon group, an alkyl group is preferable. The aliphatic hydrocarbon group may have a substituent. Examples of the substituent include groups exemplified as the above-described substituent T.

As the above-described aromatic hydrocarbon ring group, an aromatic hydrocarbon ring group having 6 to 10 carbon atoms is preferable, and a phenyl group is more preferable. The aromatic hydrocarbon ring group may have a substituent. Examples of the substituent include groups exemplified as the above-described substituent T, and an alkoxy group or the like is preferable.

$Z$, $Y^1$, $Y^2$, and *2 in General Formula (2B) have the same meaning as $Z$, $Y^1$, $Y^2$, and *2 in General Formula (2), and the preferred aspects are also the same.

$R^2$ represents a substituent. The substituent represented by $R^2$ is not particularly limited, and examples thereof include groups exemplified as the above-described substituent T. Examples of a preferred substituent represented by $R^2$ include the same substituents represented by $R^1$ in General Formula (2A) described above.

From the viewpoint that the rate of change in HTP is more excellent, in General Formula (2), in a case where Z represents a single bond, it is preferable that a carbonyl carbon specified in General Formula (2) is not bonded to —O—. That is, for example, in a case where the group represented by General Formula (2) represents the group represented by General Formula (2A), in the substituent represented by $R^1$ in General Formula (2A), it is preferable that an atom bonded to the carbonyl carbon specified in General Formula (2) is not an oxygen atom (ether oxygen). In addition, in a case where the group represented by General Formula (2) represents the group represented by General Formula (2B), it is preferable that an atom to which *2 in General Formula (2B) is bonded is not an oxygen atom (ether oxygen).

In General Formula (2), in a case where Z is a single bond, from the viewpoint that the rate of change in HTP is more excellent, the carbonyl carbon specified in General Formula (2) is preferably bonded to a hydrocarbon ring group which may have a substituent or a heterocyclic group which may have a substituent. That is, as the substituent including the group represented by General Formula (2), a substituent including a group represented by General Formula (3) is preferable.

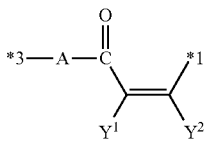

(3)

*3 in General Formula (3) represents a bonding position.

$Y^1$, $Y^2$, and *1 in General Formula (3) have the same meaning as $Y^1$, $Y^2$, and *1 in General Formula (2), and the preferred aspects are also the same.

In General Formula (3), A represents a hydrocarbon ring group which may have a substituent r a heterocyclic group which may have a substituent.

Examples of the hydrocarbon ring group include an aliphatic hydrocarbon ring group and an aromatic hydrocarbon ring group. The number of ring members of a hydrocarbon ring constituting the hydrocarbon ring group is not particularly limited, but is preferably 5 to 10.

The aliphatic hydrocarbon ring constituting the aliphatic hydrocarbon ring group may have a monocyclic structure or a polycyclic structure. In a case where the aliphatic hydrocarbon ring has a polycyclic structure, it is preferable that at least one of the rings included in the polycyclic structure is a 5- or higher membered ring.

The number of carbon atoms in the above-described aliphatic hydrocarbon ring is not particularly limited, but is preferably 5 to 10 and more preferably 5 or 6. Specific examples of the aliphatic hydrocarbon ring include a cyclopentane ring, a cyclohexane ring, a cycloheptane ring, a cyclooctane ring, a norbornene ring, and an adamantane ring. Among these, a cyclopentane ring or a cyclohexane ring is preferable.

The aromatic hydrocarbon ring constituting the aromatic hydrocarbon ring group may have a monocyclic structure or a polycyclic structure. In a case where the aromatic hydrocarbon ring has a polycyclic structure, it is preferable that at least one of the rings included in the polycyclic structure is a 5- or higher membered ring.

The number of carbon atoms in the above-described aromatic hydrocarbon ring is not particularly limited, but is preferably 6 to 18 and more preferably 6 to 10. Specific examples of the aromatic hydrocarbon ring include a benzene ring, a naphthalene ring, an anthracene ring, a phenanthrene ring, and a fluorene ring. Among these, a benzene ring or a naphthalene ring is preferable, and a benzene ring is more preferable.

Examples of the heterocyclic group include an aliphatic heterocyclic group and an aromatic heterocyclic group. The number of ring members of a heterocyclic ring constituting the heterocyclic group is not particularly limited, but is usually 5 to 10.

The aliphatic heterocyclic ring constituting the aliphatic heterocyclic group may have a monocyclic structure or a polycyclic structure. In a case where the aliphatic heterocyclic ring has a polycyclic structure, it is preferable that at least one of the rings included in the polycyclic structure is a 5- or higher membered ring.

Examples of a hetero atom included in the above-described aliphatic heterocyclic ring include a nitrogen atom, an oxygen atom, and a sulfur atom. The number of ring members in the above-described aliphatic heterocyclic ring is not particularly limited, but is preferably 5 to 10. Specific examples of the above-described aliphatic heterocyclic ring include an oxolane ring, an oxane ring, a piperidine ring, and a piperazine ring. In the aliphatic heterocyclic ring, —$CH_2$— constituting the ring may be replaced with —CO—, and examples thereof include a phthalimide ring.

The aromatic heterocyclic ring constituting the aromatic heterocyclic group may have a monocyclic structure or a polycyclic structure. In a case where the aromatic heterocyclic ring has a polycyclic structure, it is preferable that at least one of the rings included in the polycyclic structure is a 5- or higher membered ring.

Examples of a hetero atom included in the above-described aromatic heterocyclic group include a nitrogen atom, an oxygen atom, and a sulfur atom. The number of ring members in the above-described aromatic heterocyclic ring is not particularly limited, but is preferably 5 to 18. Specific examples of the above-described aromatic heterocyclic ring include a pyridine ring, a pyridazine ring, a pyrimidine ring, a pyrazine ring, a triazine ring, a thiophene ring, a thiazole ring, and an imidazole ring.

The hydrocarbon ring group and heterocyclic group represented by A may further have a substituent. The substituent is not particularly limited, and examples thereof include groups exemplified as the above-described substituent T.

As the group represented by General Formula (3), in a case where *1 is a bonding position, a group represented by General Formula (3A) is preferable, and in a case where *3 is a bonding position, a group represented by General Formula (3B) is preferable. Among these, as the group represented by General Formula (3), a group represented by General Formula (3A) is more preferable.

A, $Y^1$, $Y^2$, and *1 in General Formula (3A) have the same meaning as A, $Y^1$, $Y^2$, and *1 in General Formula (3), and the preferred aspects are also the same.

$R^3$ represents a hydrogen atom or a substituent. The substituent represented by $R^3$ is not particularly limited, examples thereof include groups exemplified as the above-described substituent T, and an alkoxy group or the like is preferable.

A, $Y^1$, $Y^2$, and *3 in General Formula (3B) have the same meaning as A, $Y^1$, $Y^2$, and *3 in General Formula (3), and the preferred aspects are also the same. $R^4$ in General Formula (3B) has the same meaning as $R^2$ in General Formula (2B), and the preferred aspect is also the same.

In a case where Z is a single bond and the group adjacent to Z is a hydrocarbon ring group which may have a substituent or a heterocyclic group which may have a substituent (that is, a case where the specific compound has the substituent including the group represented by General Formula (3)), since the leveling of the mesogen portion is further increased and the aspect ratio after exposure is increased, it is presumed that HTP is larger (that is, the rate of change in HTP is large). On the other hand, in a case where Z is —O—, it is considered that the molecular structure after exposure is twisted as compared with the case where Z is a single bond. Therefore, in a case where Z is —O—, as compared with the case where Z is a single bond, even in a case where the group adjacent to Z is a hydrocarbon ring group which may have a substituent or a heterocyclic group which may have a substituent, the leveling of the mesogen portion is difficult to improve and the rate of change in HTP is not large.

From the viewpoint that the rate of change in HTP is excellent, it is preferable that, in General Formula (1), at least one of the substituents including the group represented by General Formula (2) is linked to a binaphthyl skeleton site specified in General Formula (1) at the bonding position represented by *1. That is, it is preferable that the above-described substituent including the group represented by General Formula (2) is the above-described substituent including the group represented by General Formula (2A) or the above-described substituent including the group represented by General Formula (3A), and the bonding position represented by *1 in General Formula (2A) and General Formula (3A) is linked to the binaphthyl skeleton site specified in General Formula (1).

More specifically, the substituent including the group represented by General Formula (2) is preferably a substituent represented by General Formula (2-1), and preferably a substituent represented by General Formula (2-2).

$$*\text{-}L^A\text{-}W^A \hspace{2cm} \text{General Formula (2-1)}$$

In General Formula (2-1), $L^A$ represents a single bond or a divalent linking group. $W^A$ represents the group represented by General Formula (2A) or (2B) described above.

The divalent linking group represented by $L^A$ is not particularly limited, and examples thereof include a divalent aliphatic hydrocarbon group (which may be linear, branched, or cyclic; a divalent aliphatic hydrocarbon group having 1 to 20 carbon atoms is preferable, and examples thereof include an alkylene group; alternatively, an alkenylene group or an alkynylene group may be included), an arylene group, —O—, —S—, —$SO_2$—, —$NR^1$—, —CO—, —N=N—, —CH=N—, and a group of a combination of two or more these groups. Here, $R^1$ represents a hydrogen atom or an alkyl group (preferably having 1 to 10 carbon atoms). A hydrogen atom in the above-described

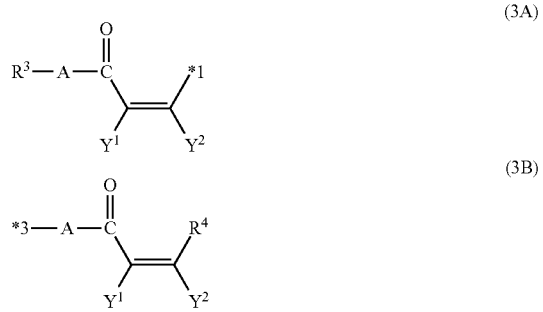

divalent linking group may be replaced with another substituent such as a halogen atom.

From the viewpoint that the rate of change in HTP is more excellent, in a case where $L^A$ represents a divalent linking group and Z in General Formula (2A) or General Formula (2B) represents a single bond, it is preferable that the bonding atom with the carbonyl carbon in $L^A$, specified in General Formula (2A) or (2B), is not an oxygen atom (ether oxygen).

As $L^A$, from the viewpoint that the rate of change in HTP is more excellent, a single bond is preferable.

In General Formula (2-1) described above, $W^A$ preferably represents the group represented by General Formula (2A).

$$*-L^B-W^B \quad \text{General Formula (2-2)}$$

In General Formula (2-2), $L^B$ represents a single bond or a divalent linking group. $W^B$ represents the group represented by General Formula (3A) or (3B) described above.

The divalent linking group represented by $L^B$ is not particularly limited, and examples thereof include a divalent aliphatic hydrocarbon group (which may be linear, branched, or cyclic; a divalent aliphatic hydrocarbon group having 1 to 20 carbon atoms is preferable, and examples thereof include an alkylene group; alternatively, an alkenylene group or an alkynylene group may be included), an arylene group, —O—, —S—, —SO$_2$—, —NR$^1$—, —CO—, —N=N—, —CH=N—, and a group of a combination of two or more these groups. Here, R$^1$ represents a hydrogen atom or an alkyl group (preferably having 1 to 10 carbon atoms). A hydrogen atom in the above-described divalent linking group may be replaced with another substituent such as a halogen atom.

As $L^B$, from the viewpoint that the rate of change in HTP is more excellent, a single bond is preferable.

In General Formula (2-2) described above, $W^B$ preferably represents the group represented by General Formula (3A).

The specific compound can be synthesized by a known method.

The specific compound may be an R-form or an S-form, or may be a mixture of R-form and S-form.

Specific examples of the specific compound will be shown below, but the specific compound is not limited thereto. In the following compounds, "Me" represents a methyl group.

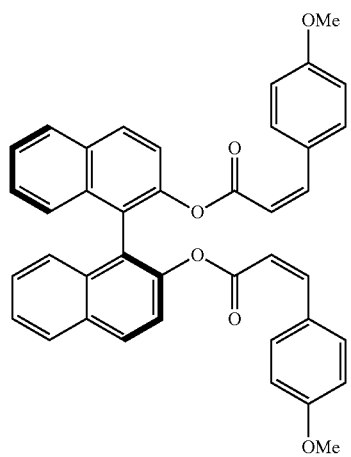

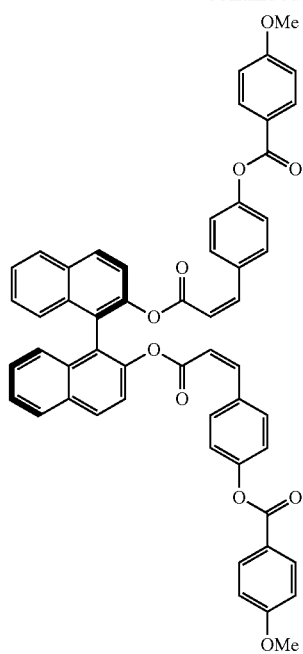

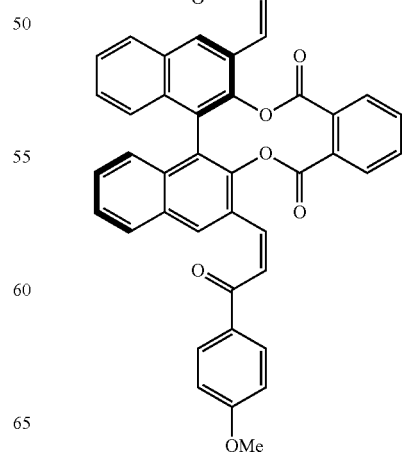

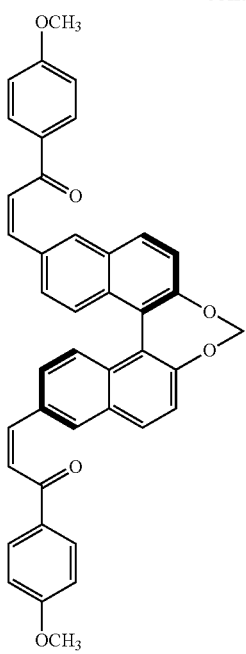
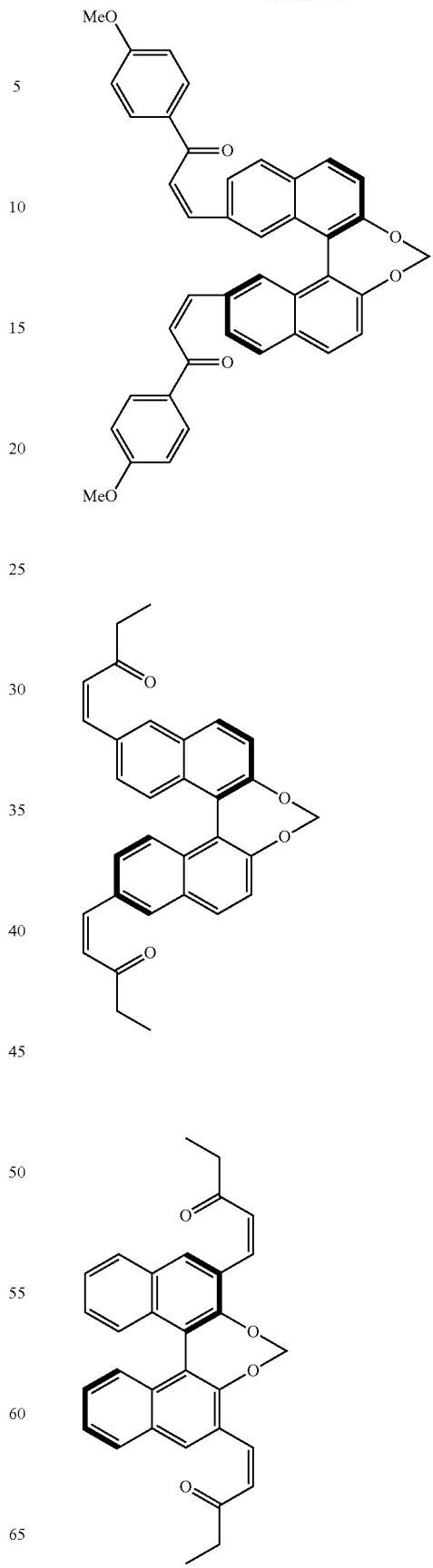

17
-continued
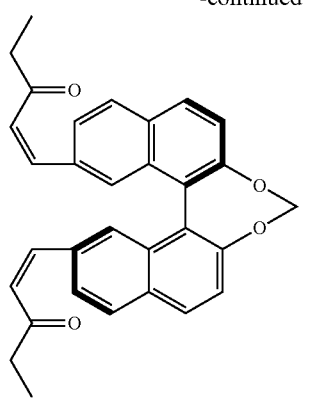
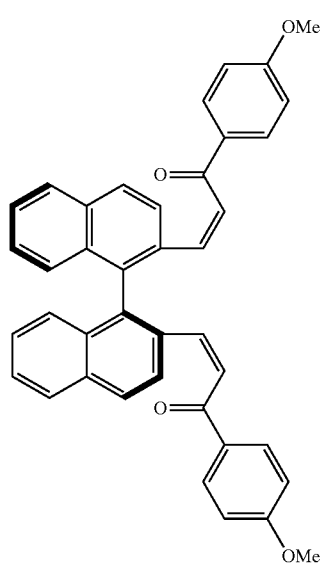
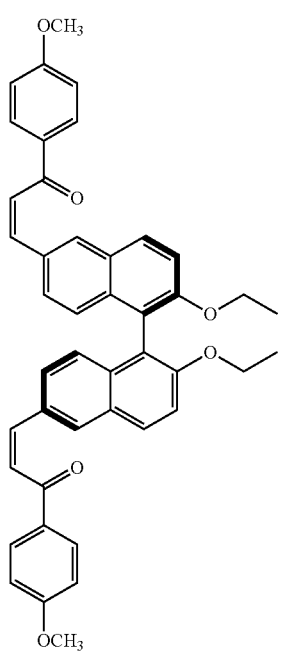
18
-continued
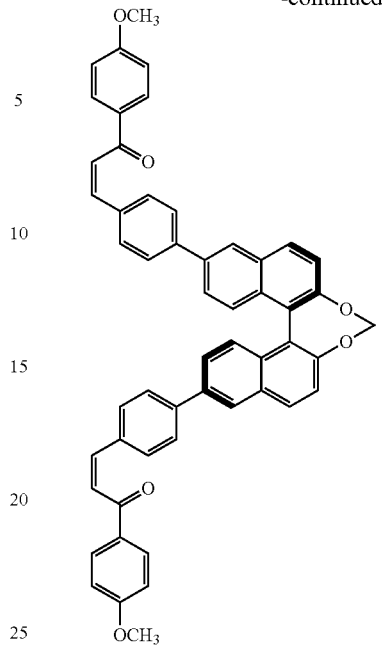
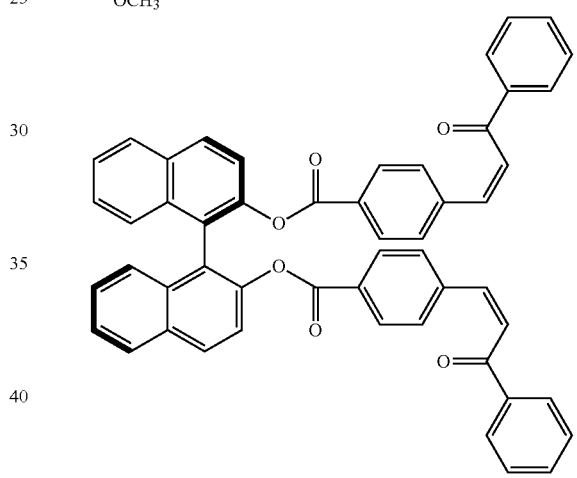
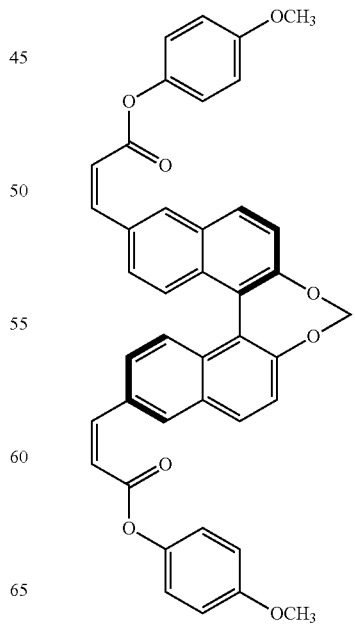

19
-continued
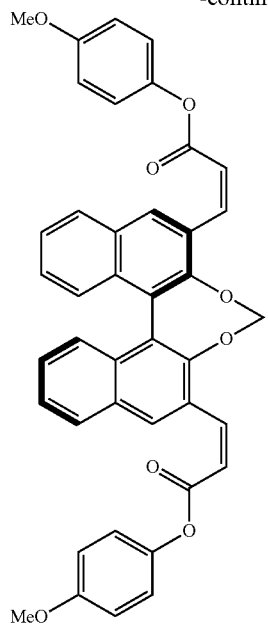
20
-continued
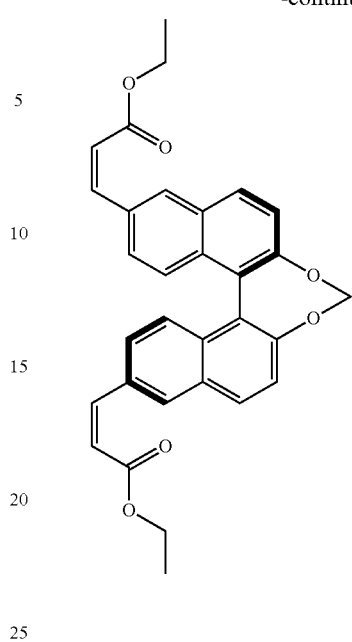
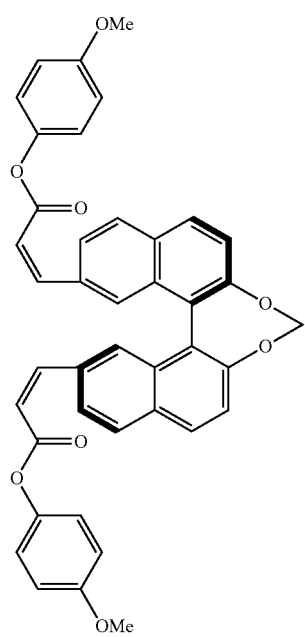
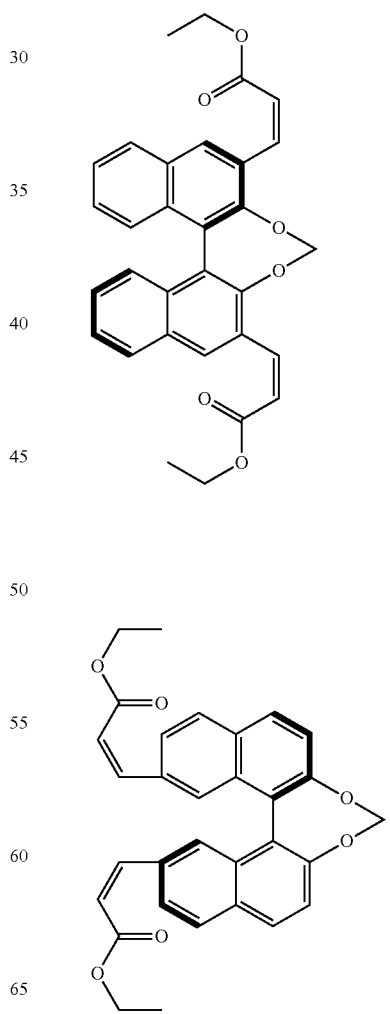

21
-continued
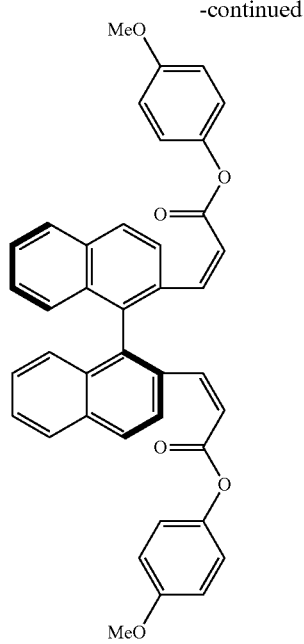
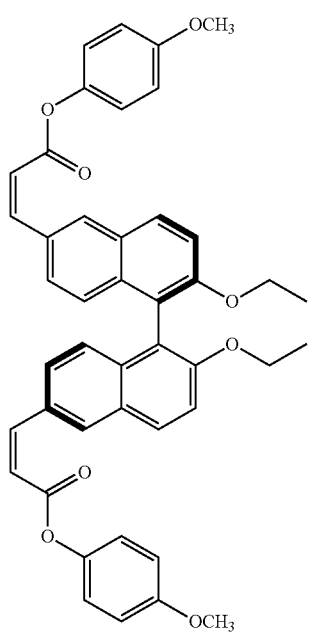
22
-continued
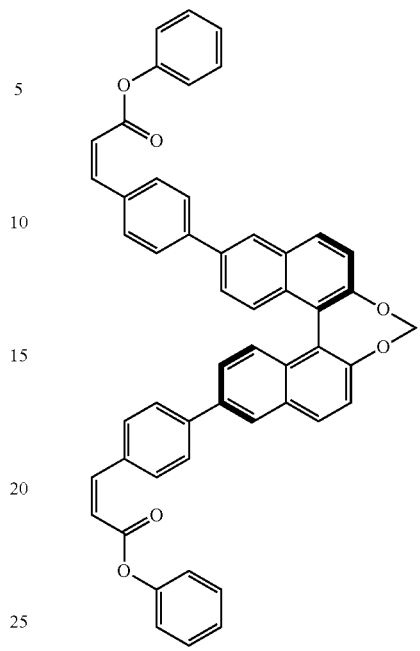
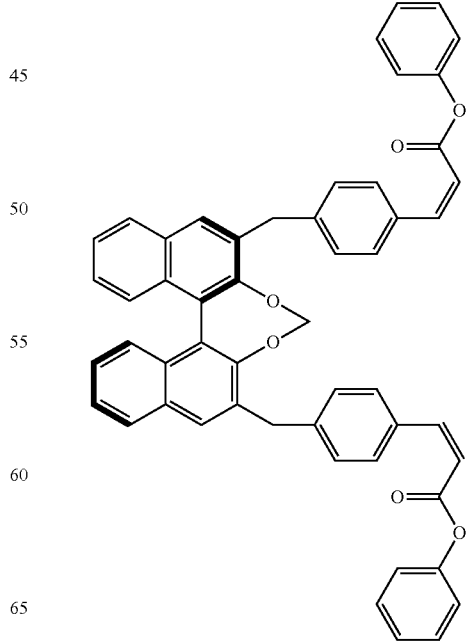

23
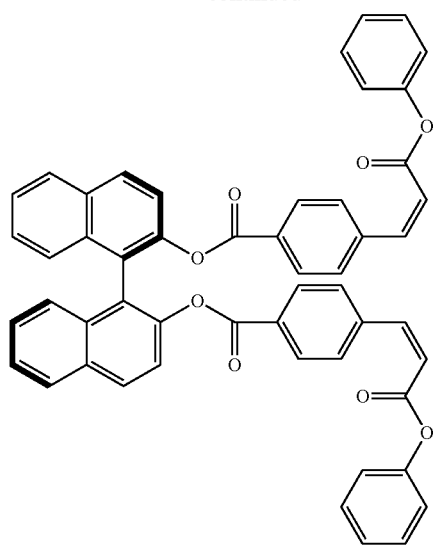
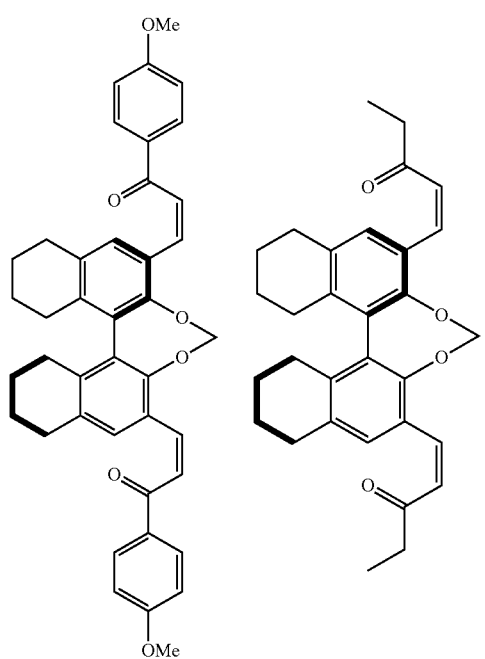
24
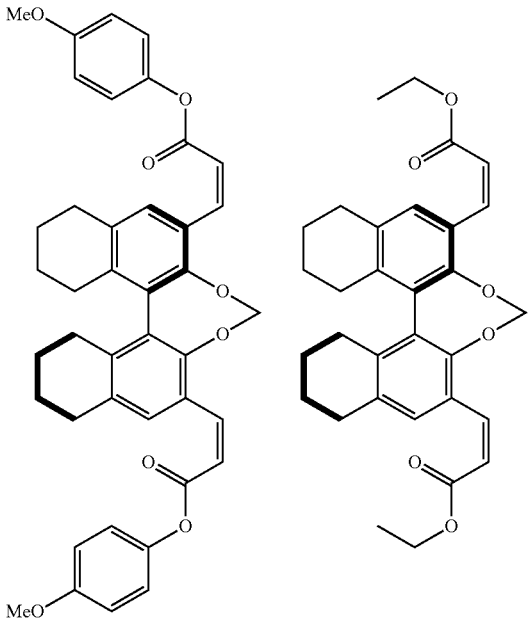
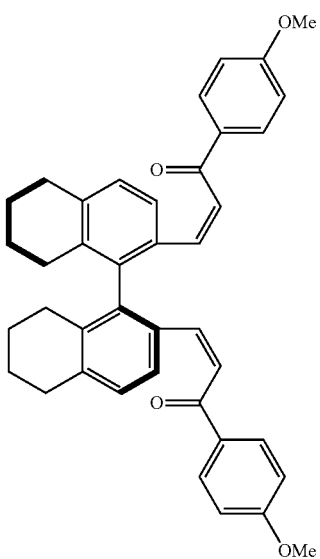

25
-continued
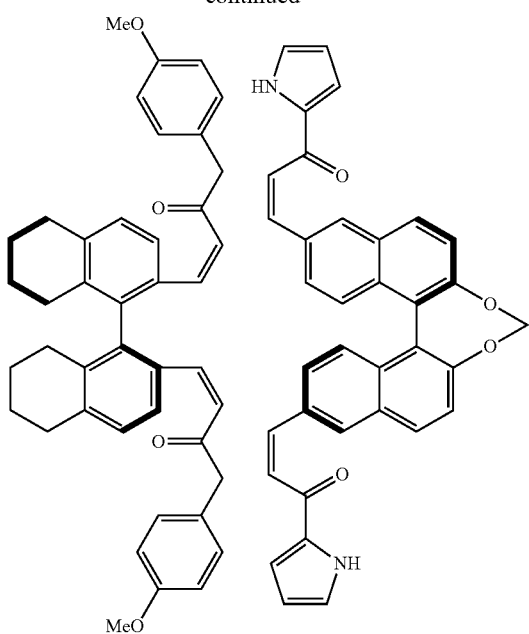
26
-continued
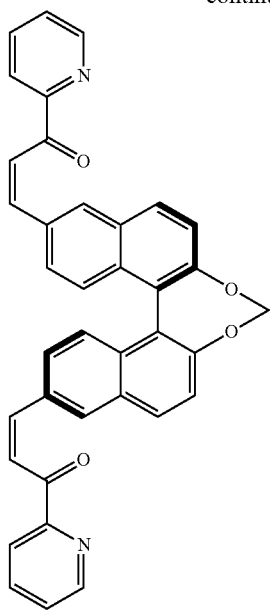
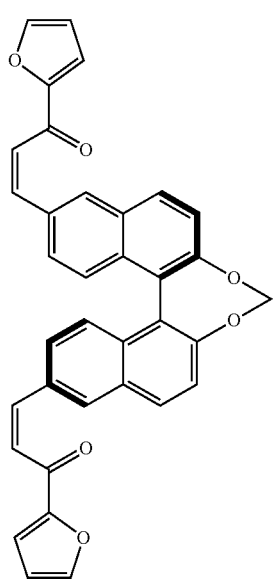
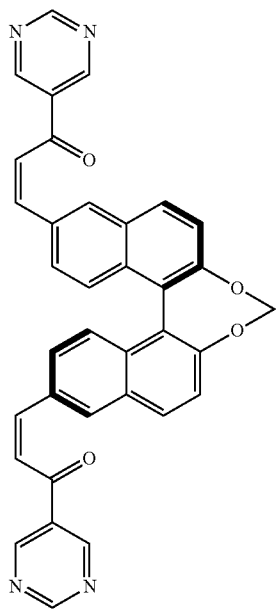

27
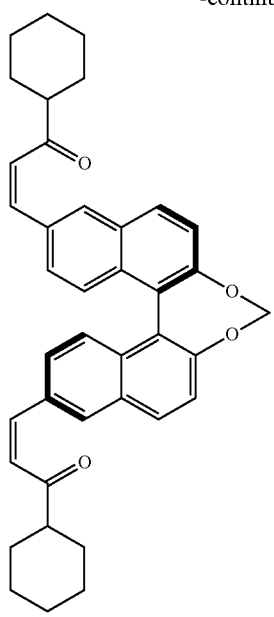
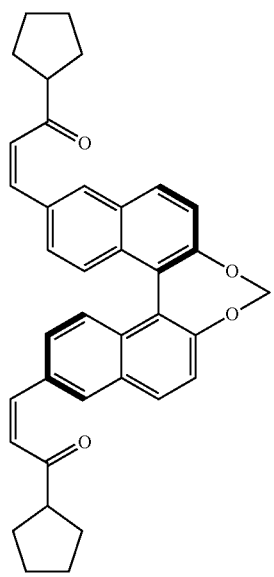
28
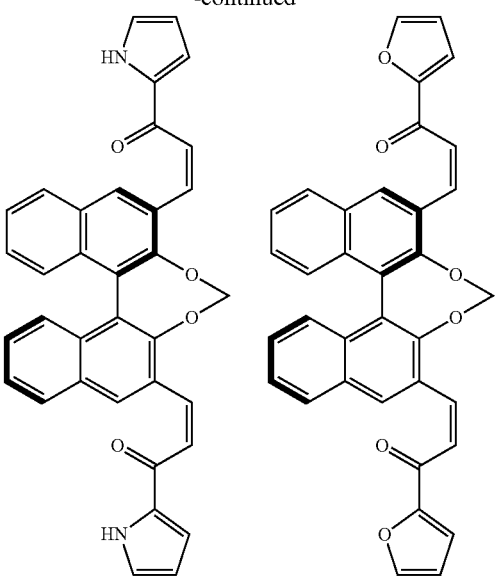
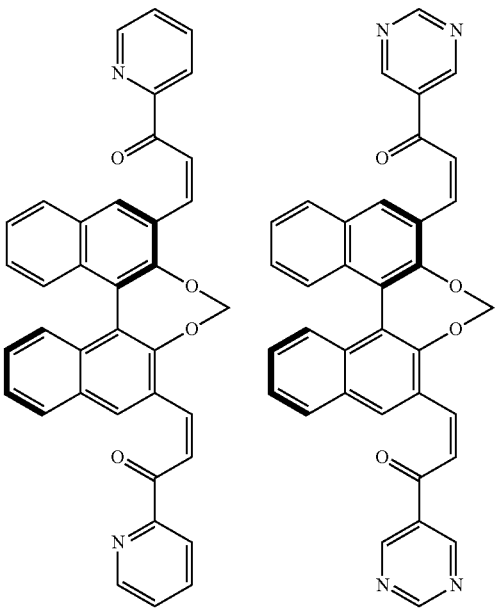

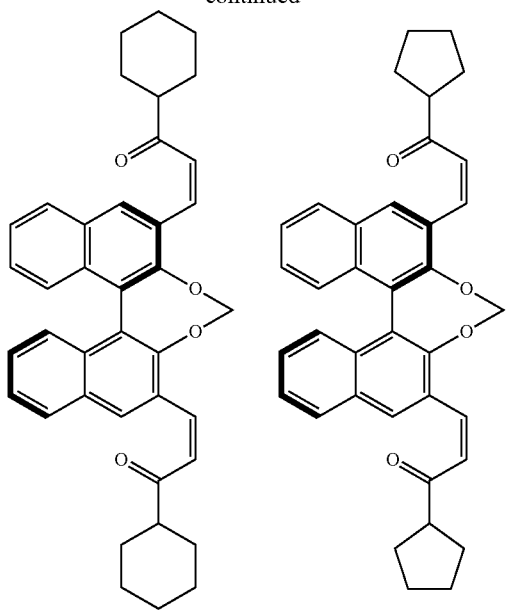
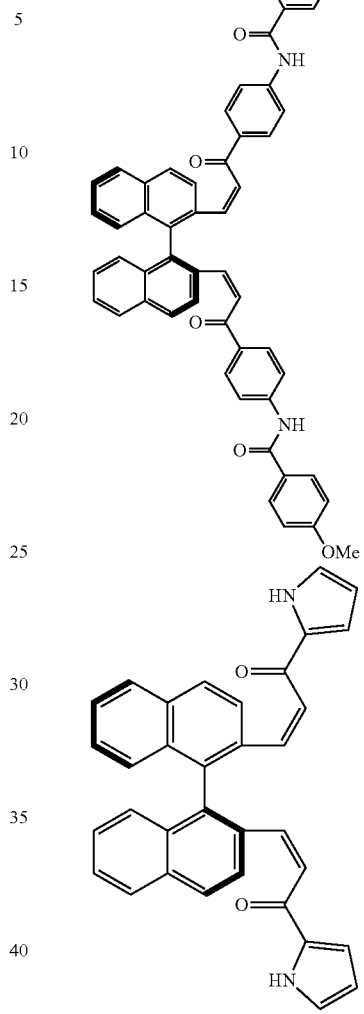
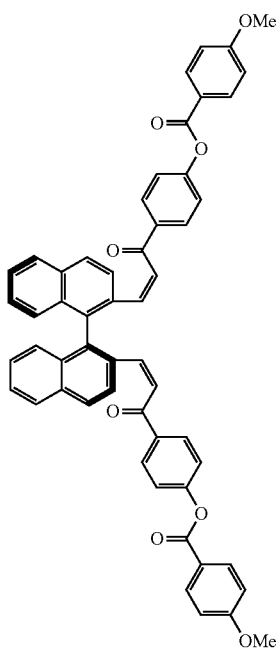

The specific compound can be applied to various uses and is suitably used as a so-called chiral compound. For example, by using a liquid crystal composition obtained by mixing the specific compound and a liquid crystalline compound, a cholesteric liquid crystalline phase can be formed.

Hereinafter, the liquid crystal composition will be described in detail.

Liquid Crystal Composition

Next, the liquid crystal composition according to the embodiment of the present invention (hereinafter, also simply referred to as a "specific liquid crystal composition") will be described.

The specific liquid crystal composition includes a specific compound and a liquid crystalline compound.

Hereinafter, various components essential or optionally contained in the specific liquid crystal composition will be described.

Specific Compound

The specific liquid crystal composition includes a specific compound. The specific compound is as described above.

The content of the specific compound in the specific liquid crystal composition is not particularly limited, but is preferably 1% to 20% by mass, more preferably 2% to 15% by mass, and still more preferably 2% to 10% by mass with respect to the total mass of the liquid crystalline compound in the composition.

In the specific liquid crystal composition, the specific compound may be used alone or in combination of two or more kinds thereof. In a case where two or more kinds thereof are used, it is preferable that the total content thereof is within the above-described range.

Liquid Crystalline Compound

The specific liquid crystal composition includes a liquid crystalline compound. The liquid crystalline compound is a compound other than the specific compound, and means a compound exhibiting liquid crystallinity.

In addition, the "compound exhibiting liquid crystallinity" is intended that the compound has properties of expressing a mesophase between a crystalline phase (low temperature side) and an isotropic phase (high temperature side) in a case of changing a temperature. As a specific observation method, optical anisotropy and fluidity derived from a liquid crystalline phase can be confirmed by performing an observation using a polarizing microscope while heating the compound or lowering a temperature of the compound with a hot stage system FP90, manufactured by METTLER TOLEDO, or the like.

The liquid crystalline compound is not particularly limited as long as it has liquid crystallinity, and examples thereof include a rod-like nematic liquid crystalline compound.

Examples of the rod-like nematic liquid crystalline compound include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolans, and alkenylcyclohexylbenzonitriles. High-molecular-weight liquid crystalline compounds can also be used as well as low-molecular-weight liquid crystalline compounds.

The liquid crystalline compound may be polymerizable or non-polymerizable, but is preferably polymerizable.

From the viewpoint that the cholesteric liquid crystalline phase can be immobilized, as the liquid crystalline compound, a liquid crystalline compound having one or more polymerizable groups is preferable, a liquid crystalline compound having two or more polymerizable groups is more preferable, and a liquid crystalline compound having two polymerizable groups is still more preferable.

Rod-like liquid crystalline compounds having no polymerizable group are described in various documents (for example, Y. Goto et al., Mol. Cryst. Liq. Cryst. 1995, Vol. 260, pp. 23 to 28).

Meanwhile, a polymerizable rod-like liquid crystalline compound is obtained by introducing a polymerizable group into the rod-like liquid crystalline compound. Examples of the polymerizable group include an unsaturated polymerizable group, an epoxy group, and an aziridinyl group. Among these, an unsaturated polymerizable group is preferable and an ethylenically unsaturated polymerizable group is more preferable. The polymerizable group can be introduced into the molecule of the rod-like liquid crystalline compound by various methods. The number of polymerizable groups included in the polymerizable rod-like liquid crystalline compound is preferably 1 to 6, more preferably 1 to 3, and still more preferably 2. Two or more kinds of polymerizable rod-like liquid crystalline compounds may be used in combination. In a case of using two or more kinds of polymerizable rod-like liquid crystalline compounds in combination, the alignment temperature can be lowered.

As the liquid crystalline compound, a compound represented by General Formula (LC) is preferable.

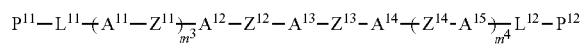

(LC)

$$P^{11}-L^{11}+(A^{11}-Z^{11})_{m^3}A^{12}-Z^{12}-A^{13}-Z^{13}-A^{14}+(Z^{14}-A^{15})_{m^4}L^{12}-P^{12}$$

In General Formula (LC), $P^{11}$ and $P^{12}$ each independently represent a hydrogen atom or a polymerizable group. However, at least one of $P^{11}$ or $P^{12}$ represents a polymerizable group. $L^{11}$ and $L^{12}$ each independently represent a single bond or a divalent linking group. $A^{11}$ to $A^{15}$ each independently represent an aromatic hydrocarbon ring group or aromatic heterocyclic group which may have a substituent. $Z^{11}$ to $Z^{14}$ each independently represent a single bond or a divalent linking group. $m^3$ and $m^4$ each independently represent an integer of 0 or 1.

In General Formula (LC), the polymerizable group represented by $P^{11}$ and $P^{12}$ is not particularly limited, and suitable specific examples thereof include the polymerizable group represented by General Formulae (P-1) to (P-20) described above. In a case where the polymerizable group represented $P^{11}$ and $P^{12}$ represents General Formulae (P-1) to (P-20) described above, * in General Formulae (P-1) to (P-20) represents a bonding position to $L^{11}$ or $L^{12}$.

It is preferable that at least any one of $P^{11}$ or $P^{12}$ represents a polymerizable group, and it is more preferable that both $P^{11}$ and $P^{12}$ represent a polymerizable group.

In General Formula (LC), the divalent linking group represented by $L^{11}$ and $L^{12}$ is not particularly limited, and examples thereof include a linear or branched alkylene group having 1 to 20 carbon atoms, and a linking group selected from the group consisting of a linear or branched alkylene group having 1 to 20 carbon atoms, in which one or two or more —$CH_2$— is replaced with —O—, —S—, —NH—, —N($CH_3$)—, —CO—, or —COO—. As the divalent linking group represented by $L^{11}$ and $L^{12}$, a group of a linear or branched alkylene group having 1 to 20 carbon atoms, in which one or two or more —$CH_2$— is replaced with —O— is preferable.

In General Formula (LC), $A^{11}$ to $A^{15}$ each independently represent an aromatic hydrocarbon ring group or aromatic heterocyclic group which may have a substituent.

The number of ring members in the above-described aromatic hydrocarbon ring group is not particularly limited, but is, for example, 5 to 10.

The aromatic hydrocarbon ring constituting the aromatic hydrocarbon ring group may have a monocyclic structure or a polycyclic structure.

The number of carbon atoms in the above-described aromatic hydrocarbon ring is not particularly limited, but is preferably 6 to 18 and more preferably 6 to 10. Specific examples of the aromatic hydrocarbon ring include a benzene ring, a biphenyl ring, a naphthalene ring, an anthracene ring, a phenanthrene ring, and a fluorene ring. Among these, a benzene ring is preferable. The above-described aromatic hydrocarbon ring constitutes an aromatic hydrocarbon ring group by removing two hydrogen atoms on the ring.

The number of ring members in the above-described aromatic heterocyclic group is, for example, 5 to 10.

The aromatic heterocyclic ring constituting the aromatic heterocyclic group may have a monocyclic structure or a polycyclic structure.

Examples of a hetero atom included in the above-described aromatic heterocyclic group include a nitrogen atom, an oxygen atom, and a sulfur atom. The number of carbon atoms in the above-described aromatic heterocyclic ring is not particularly limited, but is preferably 5 to 18. Specific examples of the above-described aromatic heterocyclic ring include a pyridine ring, a pyridazine ring, a pyrimidine ring, a pyrazine ring, a triazine ring, a thiophene ring, a thiazole ring, and an imidazole ring. The above-described aromatic heterocyclic ring constitutes an aromatic heterocyclic group by removing two hydrogen atoms on the ring.

The aromatic hydrocarbon ring group and aromatic heterocyclic group may have a substituent. The type of the substituent is not particularly limited, and examples thereof include known substituents. Examples thereof include a halogen atom, an alkyl group, an alkoxy group, an aryl group, a hydroxyl group, an amino group, a carboxyl group, a sulfonamide group, an N-sulfonylamide group, an acyl group, an acyloxy group, a cyano group, a nitro group, and an alkoxycarbonyl group. Each of the above-described groups may be further substituted with a substituent. For example, a hydrogen atom in the alkyl group may be replaced with a fluorine atom. In addition, the number of substituents is not particularly limited, and the aromatic hydrocarbon ring group and aromatic heterocyclic group may have one substituent or may have a plurality of substituents.

Among these, as the substituent, from the viewpoint that solubility of the compound represented by General Formula (LC) is further improved, a fluorine atom, a chlorine atom, a fluoroalkyl group, an alkoxy group, or an alkyl group is preferable, and a fluoroalkyl group, an alkoxy group, or an alkyl group is more preferable.

The number of carbon atoms in the fluoroalkyl group and alkyl group, and the number of carbon atoms in an alkyl group of the alkoxy group are not particularly limited, but are preferably 1 to 10, more preferably 1 to 5, still more preferably 1 to 3, and particularly preferably 1.

The fluoroalkyl group is a group in which at least one hydrogen atom in the alkyl group is replaced with a fluorine atom, and it is preferable that all hydrogen atoms are replaced with fluorine atoms (so-called perfluoroalkyl group is preferable).

As $A^{11}$ to $A^{15}$, an aromatic hydrocarbon ring group which may have a substituent is preferable, and a phenylene group bonded at the 1-position and the 4-position is more preferable.

In General Formula (LC), the divalent linking group represented by $Z^{11}$ to $Z^{14}$ is not particularly limited, and examples thereof include a divalent aliphatic hydrocarbon group (which may be any of linear, branched, or cyclic; a divalent aliphatic hydrocarbon group having 1 to 20 carbon atoms is preferable, and examples thereof include an alkylene group; in addition, an alkenylene group or an alkynylene group may be used), —O—, —S—, —SO$_2$—, —NR$^1$—, —CO—, —N=N—, —CH=N—, and a group of a combination of two or more these groups (examples of the group of a combination of two or more groups include —CO—NH—, —CO—S—, and —COO—). Here, R$^1$ represents a hydrogen atom or an alkyl group (preferably having 1 to 10 carbon atoms). A hydrogen atom in the above-described divalent linking group may be replaced with another substituent such as a halogen atom.

As $Z^{11}$ to $Z^{14}$, among these, —COO— or —CH=CH— is preferable.

In General Formula (LC), m$^3$ and m$^4$ each independently represent an integer of 0 or 1, preferably 0.

The compound represented by General Formula (LC) can be synthesized by a known method.

Specific examples of the above-described compound represented by General Formula (LC) are described below, but the compound is not limited thereto.

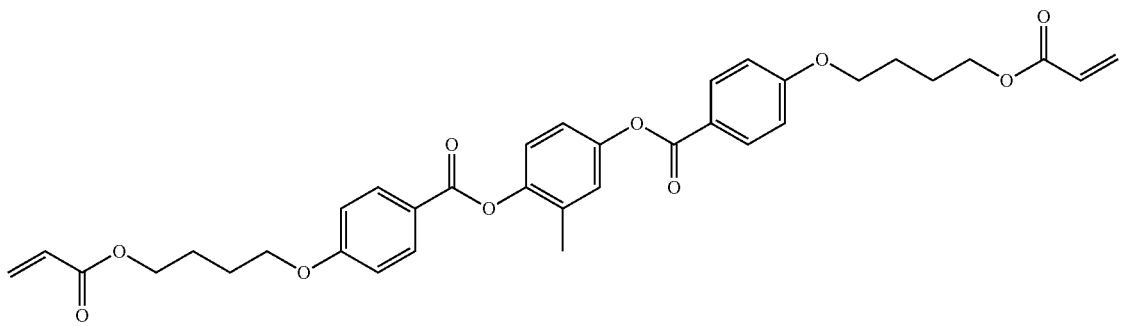

LC-1

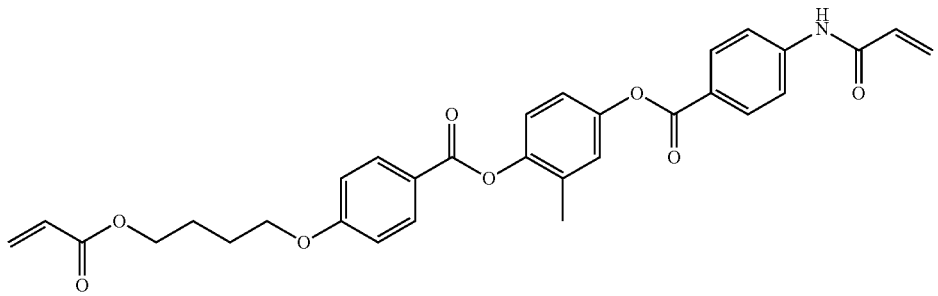

LC-2

LC-3
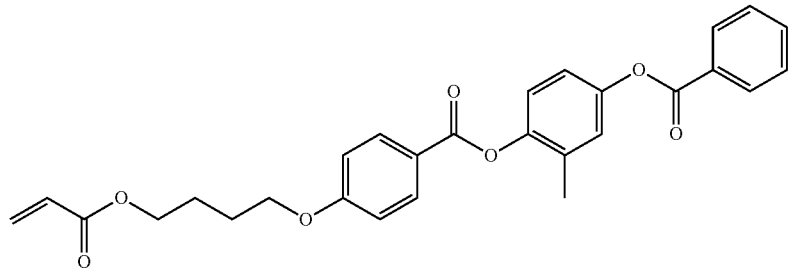
LC-4
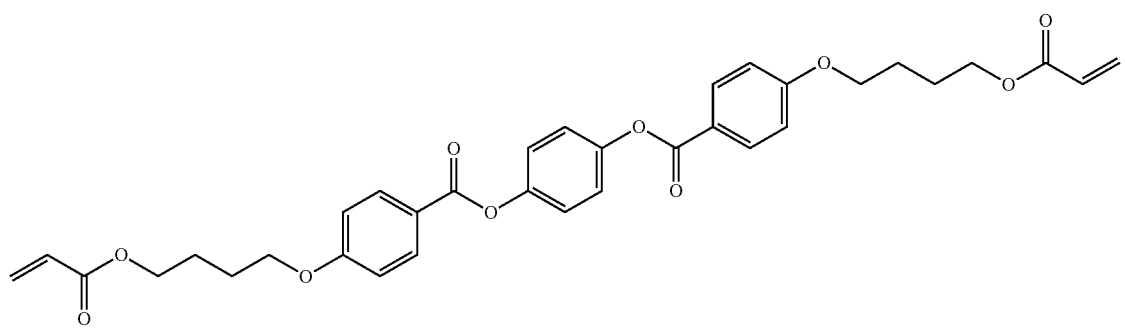
LC-5
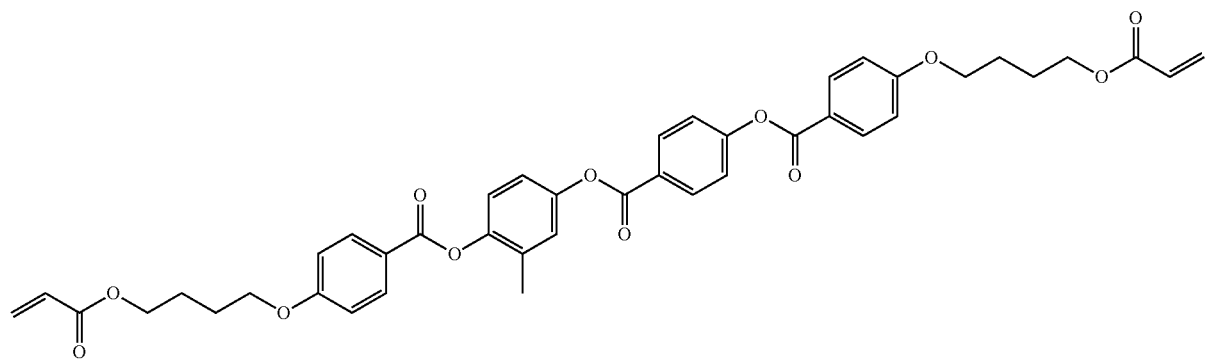
LC-6
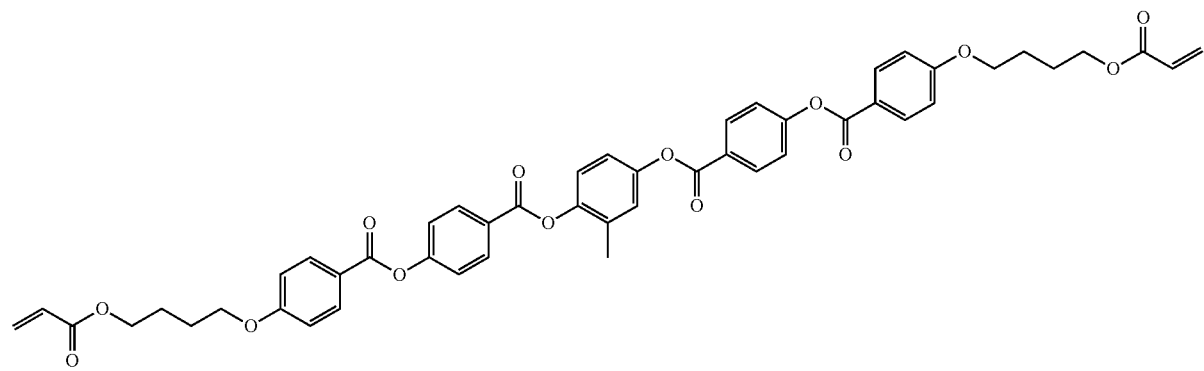

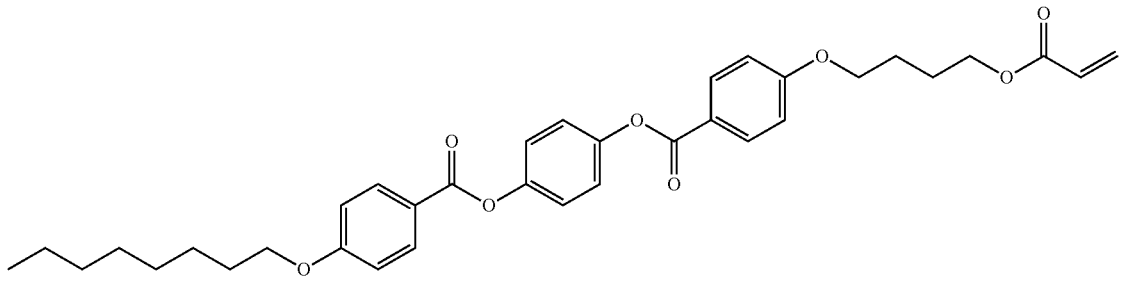

LC-7

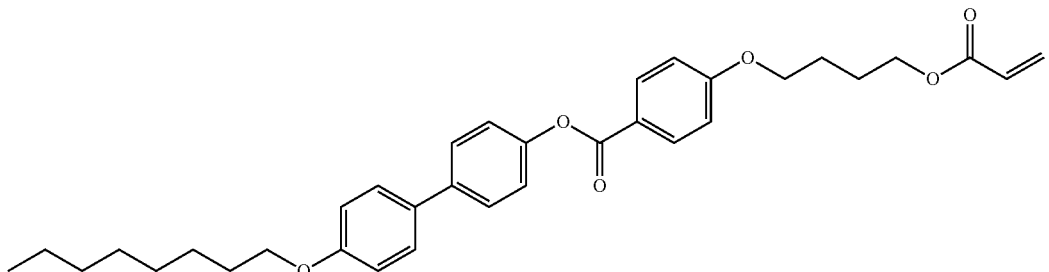

LC-8

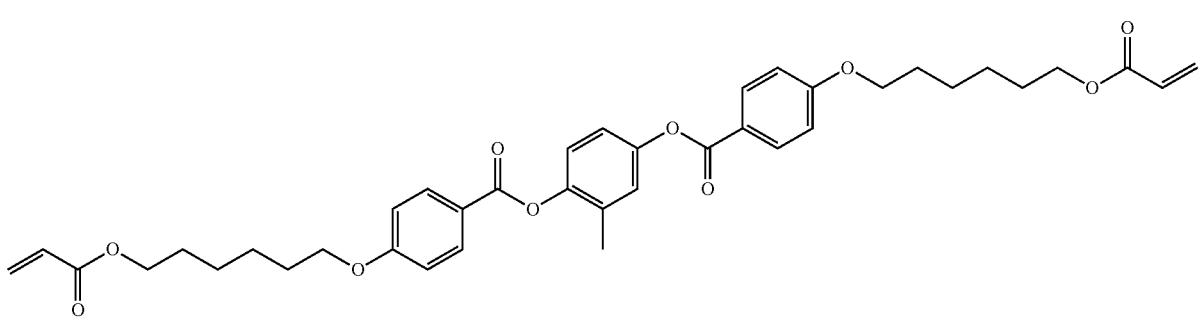

LC-9

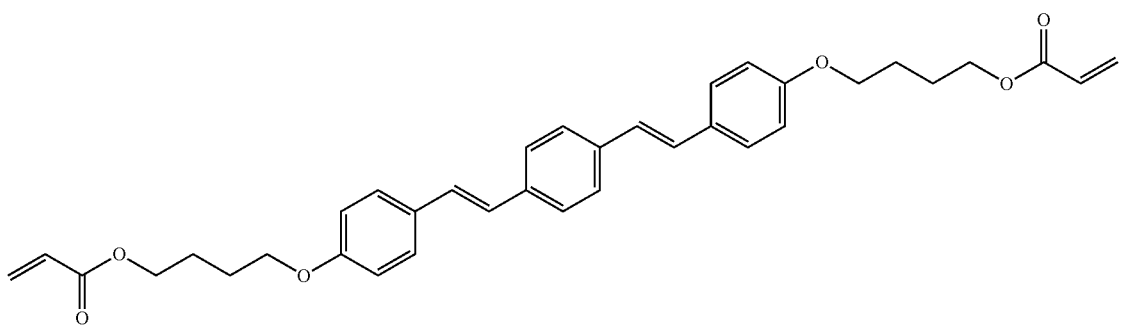

LC-10

The compound represented by General Formula (LC) may be used alone or in combination of a plurality thereof.

The content of the liquid crystalline compound in the specific liquid crystal composition is preferably 5% to 99% by mass, more preferably 25% to 98% by mass, and still more preferably 75% to 98% by mass with respect to the total solid content of the composition.

The solid contents mean components other than a solvent in the composition. In a case where a component is not a solvent, the component is regarded as a solid content even in a case where the property of the component is liquid.

In the specific liquid crystal composition, the liquid crystalline compound may be used alone or in combination of two or more kinds thereof. In a case where two or more kinds thereof are used, it is preferable that the total content thereof is within the above-described range.

Polymerization Initiator

The specific liquid crystal composition may include a polymerization initiator.

Examples of the polymerization initiator include a photopolymerization initiator and a thermal polymerization initiator. Among these, a photopolymerization initiator capable of initiating a polymerization reaction by ultraviolet irradiation is preferable. Examples of the photopolymerization initiator include an alkylphenone compound, an a-carbonyl compound, acyloin ether, an a-hydrocarbon-substituted aromatic acyloin compound, a polynuclear quinone compound, a phenazine compound, and an oxadiazole compound. As the alkylphenone compound, for example, IRGACURE 907 or the like is used.

In a case where the specific liquid crystal composition includes a polymerization initiator, the content of the polymerization initiator in the composition is not particularly limited, but is preferably 0.1% to 20% by mass and more preferably 1% to 8% by mass with respect to the total mass of the liquid crystalline compound.

In the specific liquid crystal composition, the polymerization initiator may be used alone or in combination of two or more kinds thereof. In a case where two or more kinds thereof are used, it is preferable that the total content thereof is within the above-described range.

Surfactant

The specific liquid crystal composition may include a surfactant which contributes to a stable or rapid formation of liquid crystalline phase (for example, a nematic phase and a cholesteric phase).

Examples of the surfactant include a fluorine-containing (meth)acrylate-based polymer, compounds represented by General Formulae (X1) to (X3) described in WO2011/162291A, compounds represented by General Formula (I) described in paragraphs 0082 to 0090 of JP2014-119605A, and compounds described in paragraphs 0020 to 0031 of JP2013-47204A (JP5774518B). At an air interface of a layer, these compounds can reduce a tilt angle of molecules of a liquid crystalline compound or can cause a liquid crystalline compound to be substantially horizontally aligned.

In the present specification, "horizontally aligned" means that a molecular axis of the liquid crystalline compound (which corresponds to a major axis of the liquid crystalline compound in a case where the liquid crystalline compound is a rod-like liquid crystalline compound) is parallel to a surface of the layer of the composition (film surface), but the molecular axis is not required to be strictly parallel thereto. In the present specification, the "horizontally aligned" means an alignment in which a tilt angle with the film surface is less than 20 degrees. In a case where the liquid crystalline compound is horizontally aligned near the air interface, alignment defects are less likely to occur, so that transparency in a visible light region is increased. On the other hand, in a case where the molecules of the liquid crystalline compound are aligned at a large tilt angle with respect to the film surface, for example, in a case of cholesteric phase, since a helical axis thereof deviates from a normal line of the film surface, reflectivity may decrease, fingerprint patterns may occur, or haze may increase or diffractivity may be exhibited, which are not preferable.

Examples of the fluorine-containing (meth) acrylate-based polymer which can be used as the surfactant also include polymers described in paragraphs 0018 to 0043 of JP2007-272185A.

In a case where the specific liquid crystal composition includes a surfactant, the content of the surfactant is not particularly limited, but is preferably 0.001% to 10% by mass and more preferably 0.05% to 3% by mass with respect to the total mass of the liquid crystalline compound.

In the specific liquid crystal composition, the surfactant may be used alone or in combination of two or more kinds thereof. In a case where two or more kinds thereof are used, it is preferable that the total content thereof is within the above-described range.

Solvent

The specific liquid crystal composition may include a solvent. As the solvent, a solvent which can dissolve each component of the composition is preferable. Examples thereof include methyl ethyl ketone, cyclohexanone, and a mixed solvent thereof.

In a case where the specific liquid crystal composition includes a solvent, the content of the solvent in the specific liquid crystal composition is preferably an amount at which the concentration of solid contents of the composition is 5% to 50% by mass, and more preferably an amount at which the concentration of solid contents of the composition is 10% to 40% by mass.

In the specific liquid crystal composition, the solvent may be used alone or in combination of two or more kinds thereof. In a case where two or more kinds thereof are used, it is preferable that the total content thereof is within the above-described range.

In addition to the above-described components, the specific liquid crystal composition may also include other additives such as an antioxidant, an ultraviolet absorber, a sensitizer, a stabilizer, a plasticizer, a chain transfer agent, a polymerization inhibitor, an anti-foaming agent, a leveling agent, a thickener, a flame retardant, a dispersant, a polymerizable monomer, and a coloring material such as a dye and a pigment.

Cured Product

The present invention also includes a cured product obtained by curing the specific liquid crystal composition.

Curing Method and Cured Product

A method for curing (polymerizing and curing) the specific liquid crystal composition is not particularly limited, and a known method can be adopted. Examples thereof include an aspect which includes a step X of bringing a predetermined substrate into contact with the specific liquid crystal composition to form a composition layer on the substrate, a step Y of exposing the composition layer, and a step Z of subjecting the composition layer to a curing treatment.

According to this aspect, the liquid crystalline compound can be immobilized in an aligned state, and a so-called optically anisotropic body or a layer obtained by immobilizing a cholesteric liquid crystalline phase can be formed.

Hereinafter, the procedures of steps X to Z will be described in detail.

The step X is a step of bringing a substrate into contact with the specific liquid crystal composition to form a composition layer on the substrate. The type of the substrate to be used is not particularly limited, and examples thereof include known substrates (for example, a resin substrate, a glass substrate, a ceramic substrate, a semiconductor substrate, and a metal substrate).

A method of bringing the substrate into contact with the specific liquid crystal composition is not particularly limited, and examples thereof include a method of applying the specific liquid crystal composition to the substrate and a method of immersing the substrate in the specific liquid crystal composition.

After bringing the substrate into contact with the specific liquid crystal composition, as necessary, a drying treatment may be performed in order to remove a solvent from the composition layer on the substrate. In addition, a heat treatment may be performed in order to promote the alignment of the liquid crystalline compound to be a liquid crystalline phase.

The step Y is a step of subjecting the composition layer to an exposure treatment using i-rays (wavelength: 365 nm) or the like.

In the specific compound, it is preferable that photoisomerization occurs due to the exposure treatment, so that HTP of the compound changes. In the exposure treatment, the degree of change in HTP can also be adjusted by appropriately adjusting the exposure amount, and/or the exposure wavelength and the like.

After the exposure, a heat treatment may be further performed in order to promote the alignment of the liquid crystalline compound to be a liquid crystalline phase. That is, a heat treatment may be performed in order to adjust the alignment of the liquid crystalline compound.

The helical pitch (and thus the selective reflection wavelength and the like) of the liquid crystalline phase obtained here reflects HTP adjusted in the above-described exposure treatment.

The step Z is a step of subjecting the composition layer undergone the step Y to a curing treatment.

A method of the curing treatment is not particularly limited, and examples thereof include a photo-curing treatment and a thermal-curing treatment. Among these, a photo-curing treatment is preferable.

In a case where a photo-curing treatment is performed as the curing treatment, it is preferable that the specific liquid crystal composition includes a photopolymerization initiator. The wavelength of the light irradiated in the photo-curing treatment is preferably different from the wavelength of the light used in the above-described exposure treatment, or it is preferable that the photopolymerization initiator is not sensitive to the wavelength of the light used in the exposure treatment.

By the above-described curing treatment, a layer obtained by immobilizing the cholesteric liquid crystalline phase is formed. The layer obtained by immobilizing the cholesteric liquid crystalline phase no longer needs to exhibit liquid crystallinity anymore. More specifically, for example, as a state in which the cholesteric liquid crystalline phase is "immobilized," the most typical and preferred aspect is a state in which the alignment of the liquid crystalline compound, which is the cholesteric liquid crystalline phase, is retained. More specifically, the state is preferably a state in which the layer does not exhibit fluidity within a temperature range of usually 0° C. to 50° C., and under more severe conditions of a temperature range of −30° C. to 70° C., and in which the immobilized alignment morphology can be kept stable without being changed due to an external field or an external force.

Optically Anisotropic Body and Reflective Film

The specific liquid crystal composition can be applied to various uses. For example, using the specific liquid crystal composition, a polarizer, a reflective film (reflective layer), an antireflection film, a viewing angle compensation film, a holography, a security, a sensor, a real image projection mirror (front projection and rear projection), a virtual image projection mirror, a decorative sheet, a heat-shielding sheet, a light-shielding sheet, a screen, an optically anisotropic body, an alignment film, and the like, which are a component of an optical element, can be formed. For example, in a case where the liquid crystalline compound has a polymerizable group, a cured product can be obtained by subjecting the specific liquid crystal composition to a curing treatment (such as light irradiation treatment and heat treatment), and the cured product can be suitably applied to a polarizer, a reflective film (reflective layer), an antireflection film, a viewing angle compensation film, a holography, a security, a sensor, a real image projection mirror (front projection and rear projection), a virtual image projection mirror, a decorative sheet, a heat-shielding sheet, a light-shielding sheet, a screen, an optically anisotropic body, an alignment film, and the like, which are a component of an optical element.

The optically anisotropic body is intended to be a substance having optical anisotropy.

In addition, the reflective film corresponds to a layer obtained by immobilizing the cholesteric liquid crystalline phase, and can reflect light in a predetermined reflection band.

EXAMPLES

Hereinafter, the present invention will be described in more detail based on examples. The materials, the amounts of materials to be used, the proportions, the treatment details, the treatment procedure, or the like shown in the examples below may be modified appropriately as long as the modifications do not depart from the spirit of the present invention. Therefore, the scope of the present invention should not be construed as being limited by the following examples.

Synthesis of Compound

The following shows an example of a method for synthesizing the specific compound. The compound CD-1 shown below corresponds to the compound (1) shown in Table 1 in the latter part.

Synthesis of Compound CD-1

A compound CD-1 was synthesized according to the following scheme. The compound CD-1 corresponds to the compound (1) shown in Table 1.

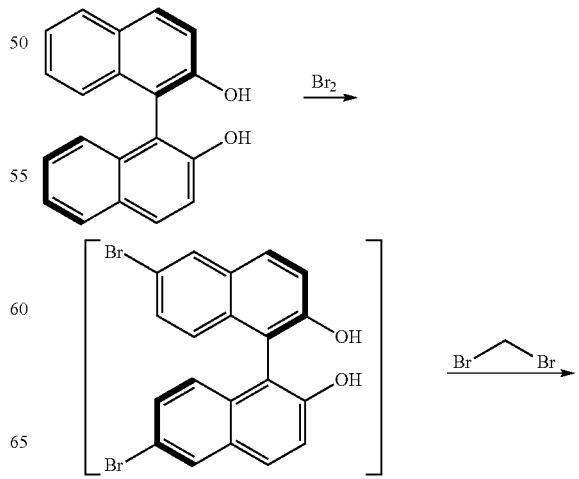

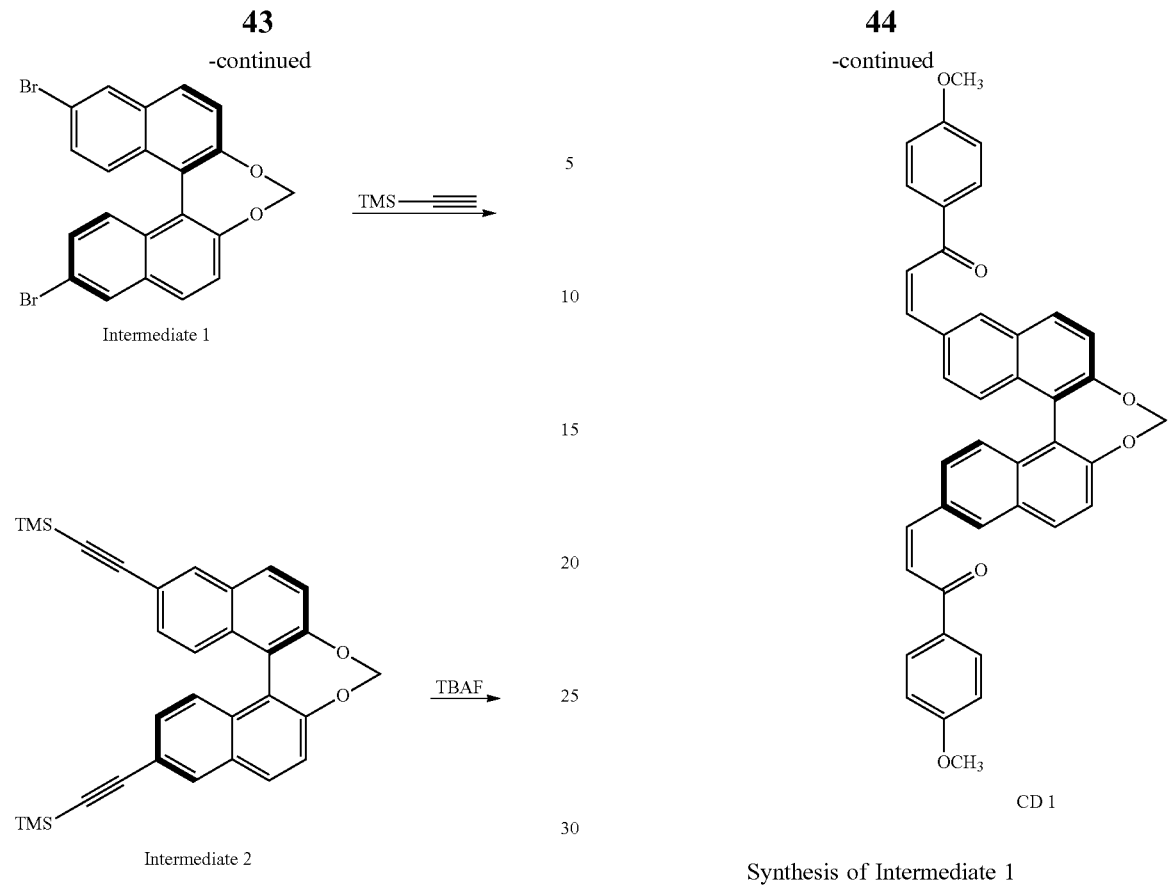

Synthesis of Intermediate 1

65.0 g of (R)-binaphthol (manufactured by KANTO CHEMICAL CO., INC.) and 500 mL of butyl acetate (manufactured by FUJIFILM Wako Pure Chemical Corporation) were charged into a 2 L three-neck flask, and then 100 g of bromine (manufactured by FUJIFILM Wako Pure Chemical Corporation) was added dropwise thereto at 0° C. and stirred for 5 hours. Subsequently, the reaction solution was washed with sodium hydrogen sulfite water (21.7 g of sodium hydrogen sulfite (manufactured by FUJIFILM Wako Pure Chemical Corporation) and 290 mL of water), 325 mL of water, and sodium hydrogen carbonate water (13.0 g of sodium hydrogen carbonate (manufactured by FUJIFILM Wako Pure Chemical Corporation) and 300 mL of water) respectively, the obtained solution was dried over magnesium sulfate, and then the solvent was distilled off under reduced pressure and transferred to a three-neck flask.

Subsequently, 80.2 g of DMF (N,N-dimethylformamide, manufactured by FUJIFILM Wako Pure Chemical Corporation), 78.0 g of potassium carbonate (manufactured by FUJIFILM Wako Pure Chemical Corporation), 75.0 g of butyl acetate (manufactured by FUJIFILM Wako Pure Chemical Corporation), and 43.5 g of dibromomethane (manufactured by FUJIFILM Wako Pure Chemical Corporation) were added thereto, and the mixture was stirred at 90° C. for 4 hours. After cooling to room temperature, the solid was filtered off, 170 mL of ethyl acetate (manufactured by FUJIFILM Wako Pure Chemical Corporation) and 550 mL of methanol (manufactured by FUJIFILM Wako Pure Chemical Corporation) were added thereto, and the resulting solid was collected by filtration and blast-dried at 40° C. for 12 hours to obtain an intermediate 1 (66.0 g, 75%).

Synthesis of Intermediate 2

60.0 g of the intermediate 1, 600 mL of tetrahydrofuran (manufactured by FUJIFILM Wako Pure Chemical Corporation), 55.8 mL of TMS acetylene (trimethylsilyl acetylene, manufactured by FUJIFILM Wako Pure Chemical Corporation), and 184 mL of triethylamine (manufactured by FUJIFILM Wako Pure Chemical Corporation) were charged into a 2 L three-neck flask, and under a nitrogen atmosphere, 4.61 g of triphenylphosphine palladium dichloride (manufactured by FUJIFILM Wako Pure Chemical Corporation) and 2.51 g of copper iodide (manufactured by FUJIFILM Wako Pure Chemical Corporation) were added thereto, and then the mixture was stirred at 60° C. for 2.5 hours. After cooling to room temperature, 300 mL of ethyl acetate (manufactured by FUJIFILM Wako Pure Chemical Corporation) was added thereto, and insoluble matter was removed by Celite filtration. 1.3 L of 1 N hydrochloric acid water was added thereto to extract an organic layer, and the obtained organic layer was washed with 900 mL of 10% sodium bicarbonate water and 900 mL of 10% saline, respectively. The obtained solution was dried over magnesium sulfate, and the solvent was distilled off from the solution under reduced pressure. A solution of ethyl acetate:hexane=2:1 was added to the crude product, the mixture was stirred at room temperature, and the solid was filtered off and dried with a 40° C. blast dryer for 12 hours to obtain an intermediate 2 (59.1 g, yield: 92%).

Synthesis of Intermediate 3

Under a nitrogen atmosphere, 34.0 g of the intermediate 2 and 300 mL of tetrahydrofuran (manufactured by FUJIFILM Wako Pure Chemical Corporation) were charged into a 1 L three-neck flask and ice-cooled. 153 mL of tetrabutylammonium fluoride (1 M tetrahydrofuran solution) was added dropwise thereto, and the mixture was stirred for 1 hour. 343 mL of 0.1 M hydrochloric acid water and 343 mL of ethyl acetate were added thereto to extract an organic layer. The obtained solution was washed with 100 mL of 10% sodium bicarbonate water, 200 mL of water, and 343 mL of 10% saline, respectively. The obtained solution was dried over magnesium sulfate, and the solvent was distilled off from the solution under reduced pressure. The crude product was purified by a short column (ethyl acetate:hexane=1:1) and then purified by column chromatography (chloroform:hexane=4:6) to obtain an intermediate 3 (17.4 g, yield: 72%).

Synthesis of Intermediate 4

Under a nitrogen atmosphere, 2.00 g of the intermediate 3, 89.4 mg of copper iodide (manufactured by FUJIFILM Wako Pure Chemical Corporation), 166 mg of triphenylphosphine palladium dichloride (manufactured by Tokyo Chemical Industry Co., Ltd.), 1.6 mL of triethylamine (manufactured by FUJIFILM Wako Pure Chemical Corporation), 40 mL of tetrahydrofuran (manufactured by FUJIFILM Wako Pure Chemical Corporation), and 2.1 mL of 4-methoxybenzoyl chloride (manufactured by Tokyo Chemical Industry Co., Ltd.) were charged into a 200 mL three-neck flask, and the mixture was stirred at 35° C. for 3.5 hours. 100 mL of ethyl acetate (manufactured by FUJIFILM Wako Pure Chemical Corporation) and 100 mL of 0.1 N hydrochloric acid water were added thereto to extract an organic layer, and the obtained solution was washed 3 times with 50 mL of saturated saline. The obtained solution was dried over magnesium sulfate, and the solvent was distilled off from the solution under reduced pressure. The crude product was purified by column chromatography (ethyl acetate:hexane=3:7) to obtain an intermediate 4 (1.66 g, yield: 49%).

Synthesis of CD-1

201 mg of the intermediate 4, 346 mg of Lindlar catalyst (manufactured by FUJIFILM Wako Pure Chemical Corporation), and 8.0 mL of 1,4-dioxane (manufactured by FUJIFILM Wako Pure Chemical Corporation) were charged into a 50 mL eggplant flask, and the mixture was replaced with hydrogen and stirred at 50° C. for 4 hours. The solid was filtered off by Celite filtration to distill off the solvent, and then purified by column chromatography (ethyl acetate:hexane=1:1) to obtain CD-1 (110 mg, 54%).

$^1$H NMR(d-DMSO) δ8.10 (2H, d), 8.05 (2H, d), 7.93 (4H, d), 7.52 (2H, d), 7.31 (2H, dd), 7.18 (2H, d), 7.05 (2H, d), 6.99 (4H, d), 6.89 (2H, d), 5.67 (2H, s), 3.78 (6H, s)

Synthesis of Compound CD-2

A compound CD-2 was synthesized according to the following scheme.

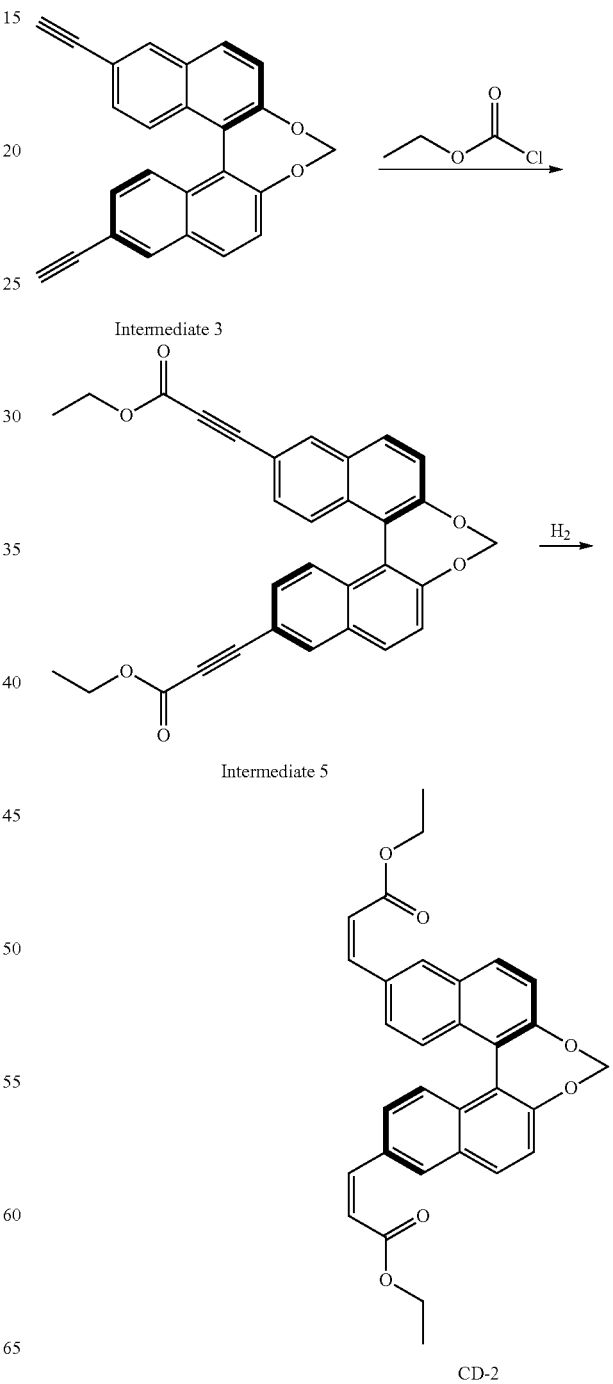

Synthesis of Intermediate 5

2.00 g of the intermediate 3 and 50 mL of tetrahydrofuran (manufactured by FUJIFILM Wako Pure Chemical Corporation) were charged into a 300 mL three-neck flask, and at −60° C., 9.5 mL of n-butyllithium (1.6 M hexane solution, manufactured by FUJIFILM Wako Pure Chemical Corporation) was added thereto. After stirring for 1 hour, 1.4 mL of ethyl chloroformate (manufactured by FUJIFILM Wako Pure Chemical Corporation) was added thereto, and the mixture was stirred for 3 hours. 200 mL of ethyl acetate (manufactured by FUJIFILM Wako Pure Chemical Corporation) was added to the reaction solution to extract an organic layer, and the obtained solution was washed 2 times with 100 mL of saturated saline. The obtained solution was dried over magnesium sulfate, and the solution was distilled off under reduced pressure. The crude product was purified by column chromatography (ethyl acetate:hexane=4:6) to obtain an intermediate 5 (1.52 g, 53%).

Synthesis of CD-2

251 mg of the intermediate 5, 55 mg of Lindlar catalyst (manufactured by FUJIFILM Wako Pure Chemical Corporation), 1.8 mL of quinoline (manufactured by FUJIFILM Wako Pure Chemical Corporation), and 10 mL of 1,4-dioxane (manufactured by FUJIFILM Wako Pure Chemical Corporation) were charged into a 50 mL eggplant flask, and the mixture was replaced with hydrogen and stirred for 1 hour. The solid was filtered off by Celite filtration, and then 80 mL of 1 N hydrochloric acid water was added thereto to extract an organic layer. The obtained solution was distilled off under reduced pressure to remove the solvent, and then purified by column chromatography (ethyl acetate:hexane=1:1) to obtain CD-2 (150 mg, 60%).

$^1$H NMR(d-DMSO) δ8.28 (2H, d), 8.17 (2H, d), 7.60 (4H, d), 7.30 (2H, d), 7.19 (2H, d), 6.10 (2H, d), 5.73 (2H, s), 4.12 (4H, q), 1.16 (6H, t)

Synthesis of Compounds (1) to (21)

Compounds (1) to (21) were synthesized with reference to the above-described method. Structures of the compounds (1) to (21) are shown below.

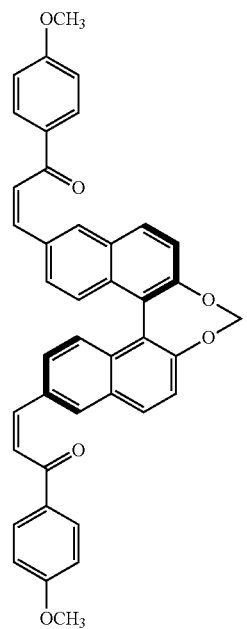

(1)

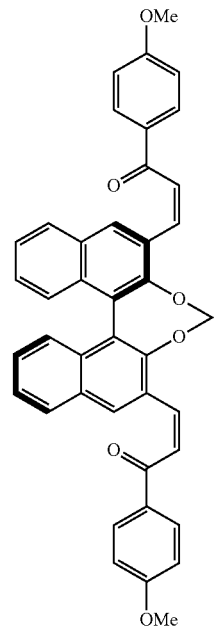

(2)

(3)
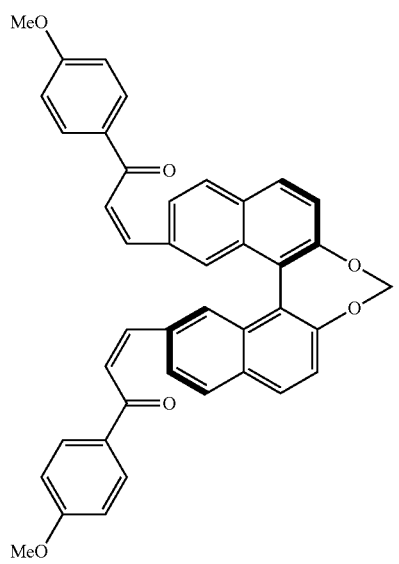
(4)
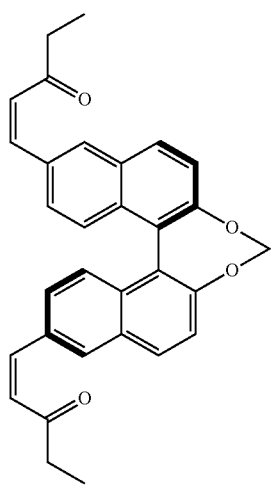
(5)
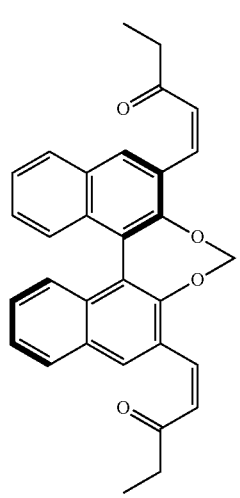
(6)
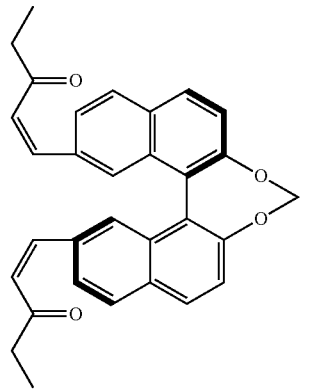
(7)
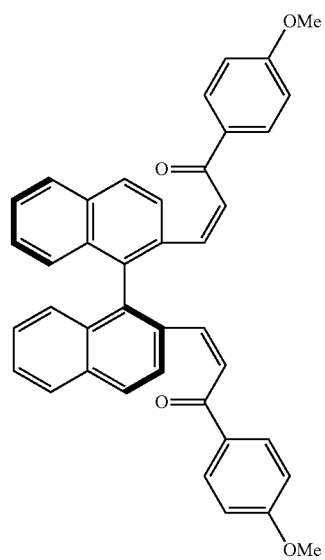
(8)
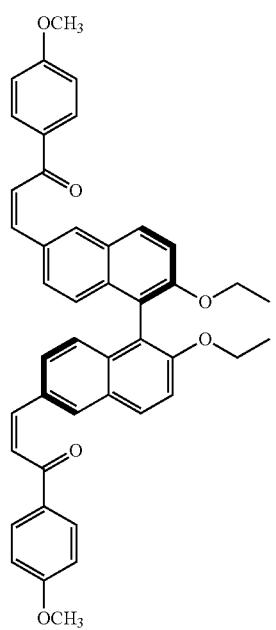

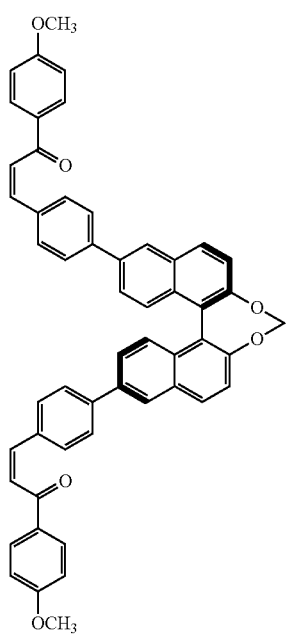
(9)
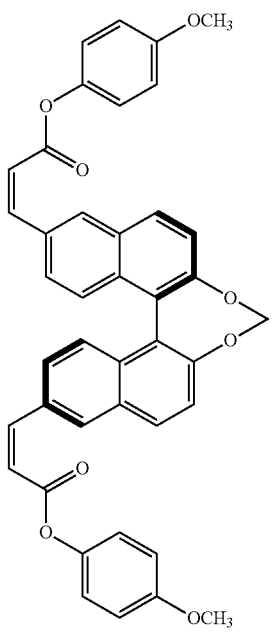
(11)
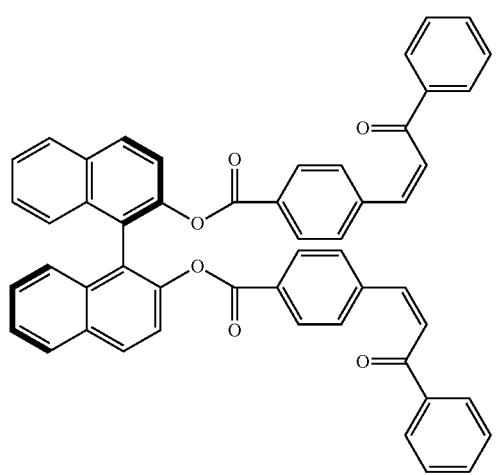
(10)
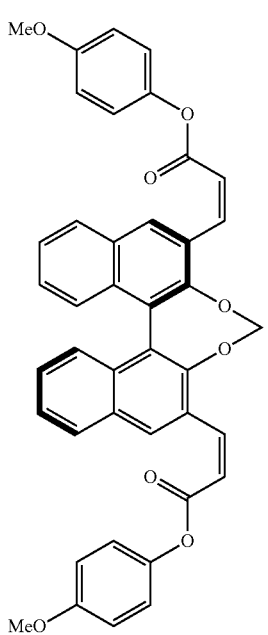
(12)

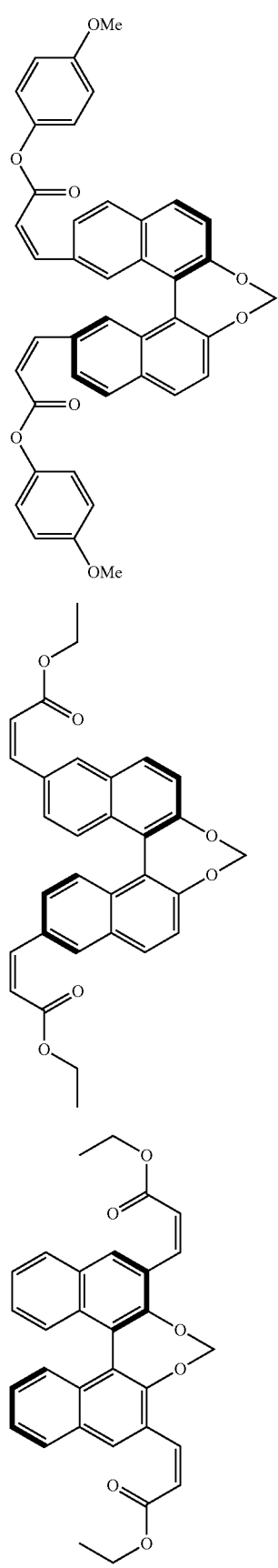
(13)
(14)
(15)
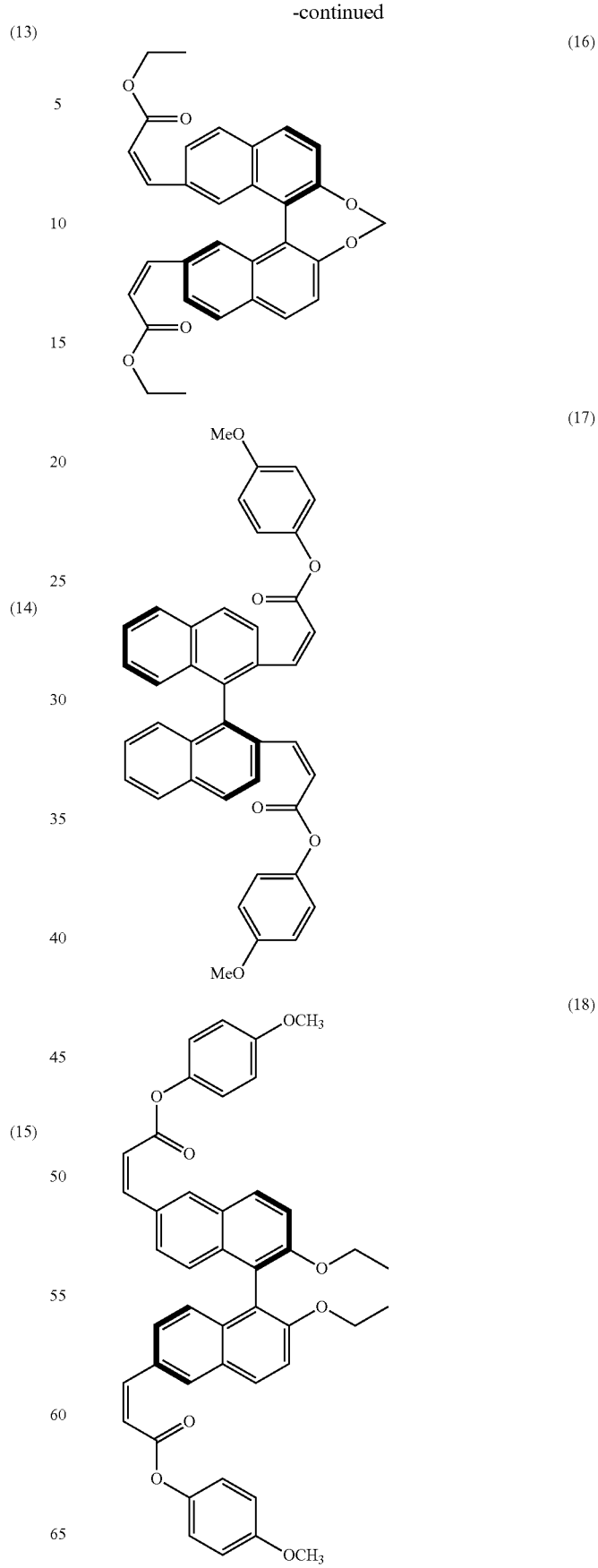
(16)
(17)
(18)

(19)

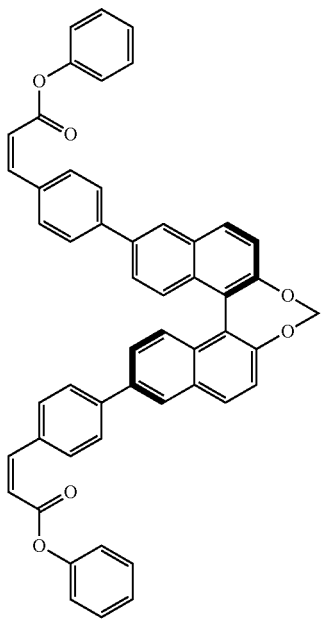

(20)

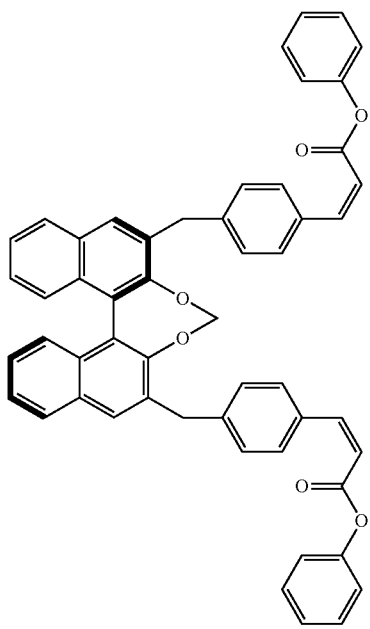

(21)

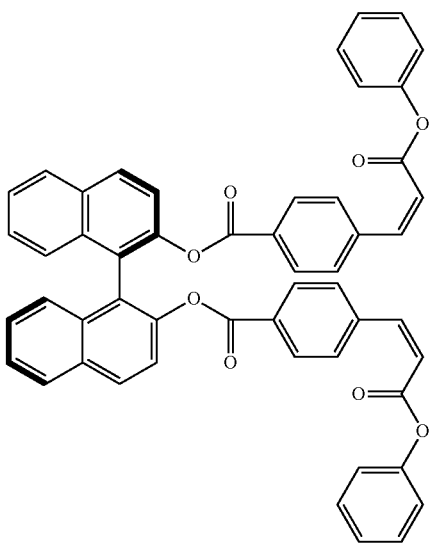

Synthesis of Compounds CE-1 to CE-3
(Comparative Compounds)

In addition, as a comparative compound, the following comparative compounds CE-1 to CE-3 were synthesized.

The compound CE-1 was a compound described in US2014/0264168A, and was synthesized according to the method described in the reference.

The compound CE-2 was a compound described in JP2007-176927A, and was synthesized according to the method described in the reference.

The compound CE-3 was a compound described in US2014/0160420A, and was synthesized according to the method described in the reference.

The structures of the compounds CE-1 to CE-3, which are comparative compounds, are shown below.

(Comparative compound CE-1)

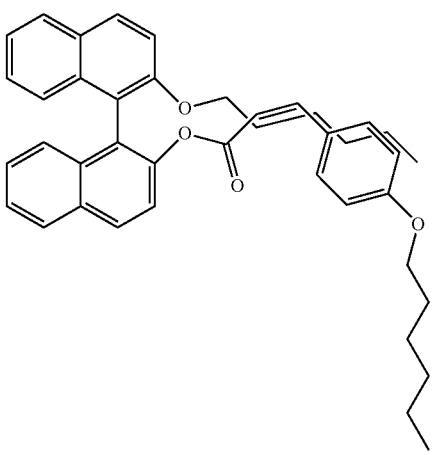

(Comparative compound CE-2)

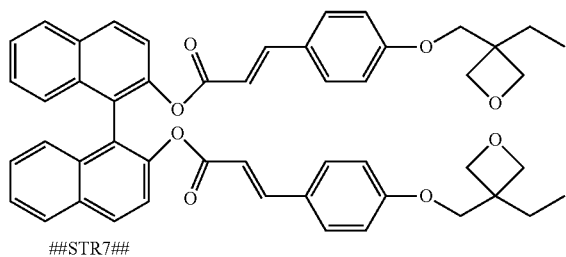

STR7##

(Comparative compound CE-3)

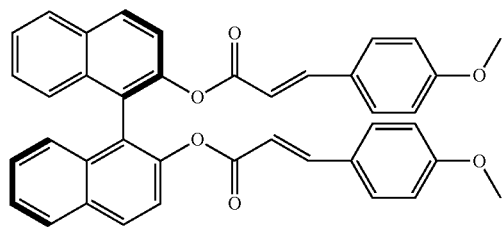

Evaluation

Evaluation of Helical Twisting Power (HTP) and Rate of Change in HTP Caused by Exposure Various compositions for evaluation were prepared with the formulations shown below.

Any one of compounds (1) to (21), or CE-1 to CE-3: 5 parts by mass

Liquid crystalline compound LC-1 shown below: 100 parts by mass

Solvent (methyl ethyl ketone (MEK)): amount at which the concentration of solid contents of the composition is 30% by mass

LC-1

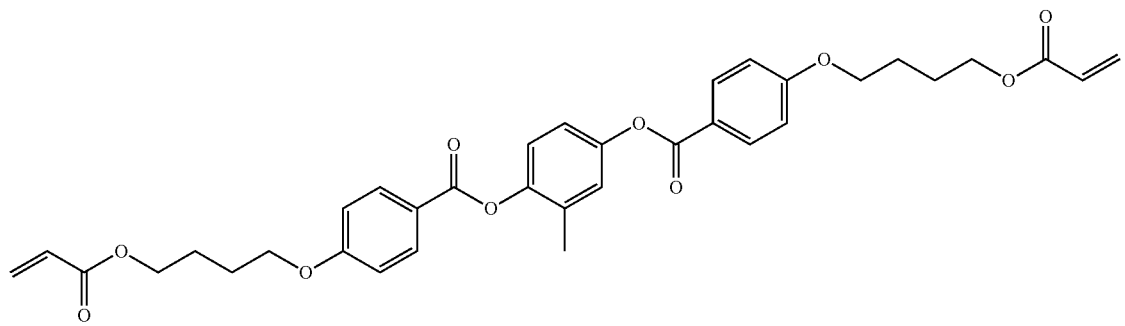

Production of Liquid Crystal Layer 1

A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film.

40 μL of the above-described composition was spin-coated on the rubbing-treated surface of the alignment film under the conditions of 1500 rpm and 10 seconds, and then the substrate was heat-dried at 90° C. for 1 minute to form a composition layer.

Regarding the obtained composition layer, the central reflection wavelength was measured at room temperature (23° C.) using a microscope (ECLIPSE E600-POL manufactured by Nikon Corporation) and a spectrophotometer (UV-3100(PC) manufactured by Shimadzu Corporation), and HTP (initial HTP) was calculated according to the following expression.

HTP [μm$^{-1}$]=(average refractive index of liquid crystalline compound)/{(concentration (% by mass) of chiral compound with respect to liquid crystalline compound)×(central reflection wavelength)}

HTP was calculated on the assumption that the average refractive index of the liquid crystalline compound was 1.55.

Furthermore, after exposing the composition layer to light having a wavelength of 365 nm (exposure amount: 150 mJ/cm$^2$), the composition layer was aged at 90° C. for 1 minute to adjust the alignment of the liquid crystal compound. Thereafter, the central reflection wavelength was measured again, and HTP after exposure was calculated in the same manner as the initial HTP using the above-described calculation expression. From the obtained initial HTP and HTP after exposure, the rate of change in HTP (rate of increase in HTP) was calculated according to the following expression.

Rate of increase in HTP [%]={(HTP after exposure)−(HTP before exposure)}/(HTP before exposure)×100

The rate of change in HTP (rate of increase in HTP) was evaluated based on the following standard. A rating is the most preferable. The results are shown in Table 1.

(Evaluation standard of rate of change in HTP (rate of increase in HTP))

"A": rate of increase in HTP was 160% or more.
"B": rate of increase in HTP was 120% or more and less than 160%.
"C": rate of increase in HTP was 80% or more and less than 120%.
"D": rate of increase in HTP was 50% or more and less than 80%.
"E": rate of increase in HTP was 30% or more and less than 50%.
"F": rate of increase in HTP was less than 30%.
"G": HTP did not increase.

The results are shown in Table 1.

In Table 1, "Substitution position of substituent including group represented by General Formula (2)" indicates which of $X^1$ to $X^8$ is the substitution position of the substituent including the group represented by General Formula (2). In the table, "X" is omitted. That is, for example, "5, 6" in Example 1 means that the substitution positions of the substituents including the group represented by General Formula (2) are $X^5$ and $X^6$.

In Table 1, in the column of "Whether or not substituent including group represented by General Formula (2) corresponds to substituent including group represented by General Formula (3)", "A" indicates a case where the substituent including the group represented by General Formula (2) corresponds to the substituent including the group represented by General Formula (3), and "B" indicates a case where the substituent including the group represented by General Formula (2) does not correspond to the substituent including the group represented by General Formula (3).

In Table 1, in the column of "Whether or not substituent including group represented by General Formula (2) is directly linked to Np ring at *1", "A" indicates that the substituent including the group represented by General Formula (2) is linked to an Np ring (binaphthyl skeleton site in General Formula (1)) at the position of *1, and "B" indicates that the substituent including the group represented by General Formula (2) is not linked to the Np ring (binaphthyl skeleton site in General Formula (1)) at the position of *1.

In Table 1, in the column of "Whether or not $X^1$ and $X^2$ are linked to each other", "A" indicates that $X^1$ and $X^2$ are linked to each other, and "B" indicates that $X^1$ and $X^2$ are not linked to each other.

TABLE 1

| | | | Characteristics of compound | | | | |
|---|---|---|---|---|---|---|---|
| | Compound No. | Type of Z | Substitution position of substituent including group represented by General Formula (2) | Whether or not substituent including group represented by General Formula (2) corresponds to substituent including group represented by General Formula (3) | Whether or not substituent including group represented by General Formula (2) is directly linked to Np ring at *1 | Whether or not $X^1$ and $X^2$ are linked to each other | Evaluation Rate of increase in HTP |
| Example 1 | Compound (1) | Single bond | 5, 6 | A | A | A | A |
| Example 2 | Compound (2) | Single bond | 3, 4 | A | A | A | A |
| Example 3 | Compound (3) | Single bond | 7, 8 | A | A | A | A |
| Example 4 | Compound (4) | Single bond | 5, 6 | B | A | A | B |
| Example 5 | Compound (5) | Single bond | 3, 4 | B | A | A | B |
| Example 6 | Compound (6) | Single bond | 7, 8 | B | A | A | B |
| Example 7 | Compound (7) | Single bond | 1, 2 | A | A | B | B |
| Example 8 | Compound (8) | Single bond | 5, 6 | A | A | B | C |
| Example 9 | Compound (9) | Single bond | 5, 6 | A | B | A | D |
| Example 10 | Compound (10) | Single bond | 1, 2 | A | B | B | D |
| Example 11 | Compound (11) | —O— | 5, 6 | B | A | A | D |
| Example 12 | Compound (12) | —O— | 3, 4 | B | A | A | D |
| Example 13 | Compound (13) | —O— | 7, 8 | B | A | A | D |
| Example 14 | Compound (14) | —O— | 5, 6 | B | A | A | C |
| Example 15 | Compound (15) | —O— | 3, 4 | B | A | A | C |
| Example 16 | Compound (16) | —O— | 7, 8 | B | A | A | C |
| Example 17 | Compound (17) | —O— | 1, 2 | B | A | B | C |
| Example 18 | Compound (18) | —O— | 5, 6 | B | A | B | E |
| Example 19 | Compound (19) | —O— | 5, 6 | B | B | A | E |
| Example 20 | Compound (20) | —O— | 3, 4 | B | B | A | E |
| Example 21 | Compound (21) | —O— | 1, 2 | B | B | B | E |
| Comparative Example 1 | Comparative compound CE-1 | — | — | — | — | — | F |
| Comparative Example 2 | Comparative compound CE-2 | — | — | — | — | — | G |
| Comparative Example 3 | Comparative compound CE-3 | — | — | — | — | — | G |

From the results in Table 1, it was confirmed that the compounds of Examples were excellent in the rate of increase in HTP caused by exposure.

In addition, from the comparison between Examples 1 to 8 and Examples 11 to 18 (each comparison of Example 1 and Example 11, Example 2 and Example 12, Example 3 and Example 13, Example 4 and Example 14, Example 5 and Example 15, Example 6 and Example 16, Example 7 and Example 17, and Example 8 and Example 18), it was confirmed that the rate of increase in HTP was more excellent in a case where, in General Formula (2), Z was a single bond.

From the comparison between Examples 1 to 3 and Examples 4 to 6 (each comparison of Example 1 and Example 4, Example 2 and Example 5, and Example 3 and Example 6), it was confirmed that the rate of increase in HTP was more excellent in a case where Z in General Formula (2) was a single bond, and the substituent including the group represented by General Formula (2) was the substituent including the group represented by General Formula (3).

From the comparison between Example 1 and Example 8, and Example 11 and Example 18, it was confirmed that the rate of increase in HTP was more excellent in a case where, in General Formula (1), $X^1$ and $X^2$ were linked to each other.

From the comparison between Example 7 and Example 8, and Example 17 and Example 18, it was confirmed that the rate of increase in HTP was more excellent in a case where, in General Formula (1), $X^1$ and $X^2$ were not linked to each other, both $X^1$ and $X^2$ represented the substituent including the group represented by General Formula (2) described above, and at least one of the substituents including the group represented by General Formula (2) was directly linked to the Np ring at the bonding position represented by *1 in the substituent.

From the comparison between Example 1 and Example 9, and Example 11, Example 19, and Example 20, it was confirmed that the rate of increase in HTP was more excellent in a case where the substituent including the group represented by General Formula (2) was directly linked to the Np ring at the bonding position represented by *1.

Comparative Example 1 did not satisfy the desired requirement because the comparative compound CE-1 had only one substituent including the group represented by General Formula (2).

Comparative Examples 2 and 3 did not satisfy the desired requirement because two hydrogen atoms on the double bond in the comparative compounds CE-2 and CE-3 were on different sides with respect to the axis of the double bond (the comparative compounds CE-2 and CE-3 correspond to the trans structure).

Production of Reflective Film

A liquid crystal composition was prepared with the formulation shown below.
Compound (1): 5 parts by mass
Liquid crystalline compound LC-1 shown above: 100 parts by mass
Surfactant S-1 shown below: 0.1 parts by mass
IRGACURE 907 (manufactured by BASF): 3 parts by mass
Solvent (methyl ethyl ketone (MEK)): amount at which the concentration of solid contents of the composition is 30% by mass The surfactant S-1 is a compound described in JP5774518B, and has the following structure.

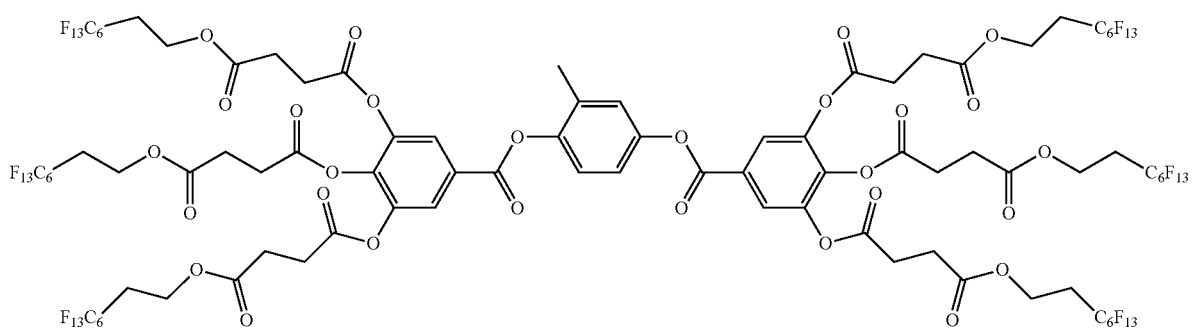

(S-1)

Production of Reflective Film

A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film. 40 µL of the above-described liquid crystal composition was spin-coated on the rubbing-treated surface of the alignment film under the conditions of a rotation speed of 1500 rpm for 10 seconds to form a composition layer. Thereafter, the composition layer was dried (aged) at 90° C. for 1 minute, thereby aligning the liquid crystalline compound in the composition layer (in other words, obtaining a composition layer in a state of the cholesteric liquid crystalline phase).

Next, the composition layer in which the liquid crystalline compound had been aligned was irradiated with light, which is emitted from a light source (2UV Transilluminator manufactured by UVP Inc.) and has a wavelength of 365 nm, at an irradiation intensity of 3.0 mW/cm² for 30 seconds through a mask having an opening portion (corresponding to the treatment of changing HTP). Due to the difference between the opening portion and the non-opening portion of the mask, the composition layer was in a state of having a portion irradiated with light having a wavelength of 365 nm and a portion not irradiated with light.

Subsequently, the composition layer was aged at 90° C. for 1 minute to adjust the alignment of the liquid crystal compound. Further, in a state of removing the mask, the composition layer was subjected to a curing treatment by irradiation with ultraviolet rays (manufactured by HOYA-SCHOTT CORPORATION, EXECURE 3000-W, 315 nm) at an irradiation amount of 500 mJ/cm² under a nitrogen atmosphere at 25° C., thereby obtaining a reflective film (corresponding to a layer obtained by immobilizing the cholesteric liquid crystalline phase).

In the obtained reflective film, it was found that the portion irradiated with light having a wavelength of 365 nm exhibited a short-wavelength reflection and the portion not irradiated exhibited a long-wavelength reflection, and that the selective reflection wavelengths were different (that the helical pitches of the cholesteric layer were different).

What is claimed is:

1. A compound represented by General Formula (1),

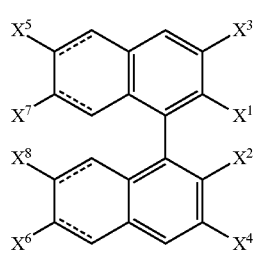

(1)

in General Formula (1), a portion where a solid line and a broken line are parallel to each other represents a single bond or a double bond, in General Formula (1) $X^1$ to $X^8$ each independently represent a hydrogen atom or a monovalent substituent, provided that at least one of $X^1$, $X^3$, $X^5$, or $X^7$ and at least one of $X^2$, $X^4$, $X^6$, or $X^8$ represent a substituent selected from the group consisting of a substituent including a group represented by General Formula (2A) and a substituent including a group represented by General Formula (3A),

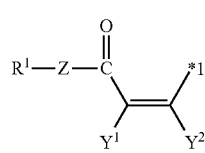

(2A)

in General Formulae (2A), Z represents a single bond or —O—, $Y^1$ and $Y^2$ each. independently represent a hydrogen atom or a hydrocarbon group not including an aryl group, and *1 represents a bonding position, and $R^1$ represents a hydrogen atom or a substituent, and the group represented by General Formula (2A) has $Y^1$ and $Y^2$ on the same side with the double bond specified h General Formula (2A) as an axis,

(3A)

in General Formula (3A). :A represents a hydrocarbon ring group which may have a substituent or a heterocyclic group which may have a substituent, $Y^1$ and $Y^2$ each independently represent a hydrogen atom or a hydrocarbon group not including, an aryl group, and *1 represents a bonding position, and $R^3$ represents a hydrogen atom or a substituent, and the group represented by General Formula (3A) has $Y^1$ and $Y^2$ on the same side with the double bond specified in General Formula (3A) as an axis, and in General Formula (1), $X^1$ and $X^2$ may be linked to each other to form a ring.

2. The compound according to claim 1, wherein, in General Formula (1), $X^1$ and $X^2$ are linked to each other to form a ring.

3. The compound according to claim 1, wherein, in General Formula (1), both $X^1$ and $X^2$ represent the substituent selected from the group consisting of the substituent including the group represented by General Formula (2A) and the substituent including the group represented. by General Formula (3A).

4. The compound according to claim 1, wherein in General Formula (2A), $R^1$ is a hydrogen atom, an aliphatic hydrocarbon group, or an aromatic hydrocarbon ring group.

5. The compound according to claim 1 wherein, in General Formula (2A), Z is a single bond, and a carbonyl carbon specified in General Formula (2A) is not bonded to —O—.

6. A liquid crystal composition comprising:
the compound according to claim 1; and
a liquid crystalline compound.

7. The liquid crystal composition according to claim 6, wherein the liquid crystalline compound includes two polymerizable groups.

8. A cured product obtained by curing the liquid crystal composition according to claim 6.

9. An optically anisotropic body obtained by curing, the liquid crystal. composition according to claim 6.

10. A reflective film obtained by curing the liquid crystal composition according to claim 6.

11. The compound according to claim 2, wherein in General Formula (2A), $R^1$ is a hydrogen atom, an aliphatic hydrocarbon group, or an aromatic hydrocarbon ring group.

12. The compound according to claim 2, wherein, in General Formula (2 A), Z is a single bond, and a carbonyl carbon specified in General Formula (2A) is not bonded to —O—.

13. A liquid crystal composition comprising:
the compound according to claim 2; and
a liquid crystalline compound.

14. The compound according to claim 1, wherein in General Formula (2A), $R^1$ is an aliphatic hydrocarbon group, or an aromatic hydrocarbon ring group, and Z is a single bond.

15. The compound according to claim 1, wherein the substituent including the group represented by General Formula (2A) is a substituent represented by General Formula (2-1), and the substituent including the group represented by General Formula (3A) is a substituent represented by General Formula (2-2), General Formula (2-1): *-$L^A$-$W^A$ in General Formula (2-1), $L^A$ represents a single bond or a divalent linking group, and $W^A$ represents the group represented by General Formula (2A), General Formula (2-2): *-$L^B$-$W^B$ in General Formula (2-2), $L^B$ represents a single bond or a divalent linking group, and $W^B$ represents the group represented by General Formula (3A).

* * * * *